US005830479A

United States Patent [19]
Emery et al.

[11] Patent Number: 5,830,479
[45] Date of Patent: Nov. 3, 1998

[54] ACTIVE IMMUNIZATION USING A SIDEROPHORE RECEPTOR PROTEIN

[75] Inventors: Daryll A. Emery; Darren E. Straub; Richard Huisinga, all of Willmar; Beth A. Carlson, Murdock, all of Minn.

[73] Assignee: Willmar Poultry Company, Inc., Willmar, Minn.

[21] Appl. No.: 385,273

[22] Filed: Feb. 8, 1995

Related U.S. Application Data

[63] Continuation-in-part of Ser. No. 194,040, Feb. 9, 1994, abandoned.

[51] Int. Cl.$^6$ .......................... A61K 39/102; A61K 39/02; A61K 39/116; A61K 39/108
[52] U.S. Cl. ..................... 424/255.1; 424/184.1; 424/203.1; 424/282.1; 424/93.3; 424/826; 424/823; 424/824; 424/241.1
[58] Field of Search .............................. 424/203.1, 255.1, 424/257.1, 241.1, 258.1, 282.1, 93.3

[56] References Cited

U.S. PATENT DOCUMENTS

| | | | |
|---|---|---|---|
| 4,452,775 | 6/1984 | Kent | 424/19 |
| 4,626,416 | 12/1986 | DeVoe et al. | 423/12 |
| 4,663,161 | 5/1987 | Mannino et al. | 424/89 |
| 4,681,761 | 7/1987 | Mietzner et al. | 424/92 |
| 4,748,018 | 5/1988 | Stolle et al. | 424/87 |
| 4,871,488 | 10/1989 | Mannino et al. | 424/89 |
| 5,141,743 | 8/1992 | Schryvers | 424/88 |
| 5,292,869 | 3/1994 | Schryvers | 530/413 |
| 5,587,166 | 12/1996 | Donachie | 424/255.1 |

FOREIGN PATENT DOCUMENTS

| | | | |
|---|---|---|---|
| 2029906 | 9/1990 | Canada | C12P 21/00 |
| 2049906 | 9/1990 | Canada | C12P 21/00 |

OTHER PUBLICATIONS

Bolin et al, Infection & Immunity 55:1239–1242, 1987.
Klebba et al, Journal of Bacteriology 149:880–888, 1982.
Neilands Ann Rev Microbiol 36:285–309, 1982.
Erdel et al. Infection & Immunity 62:1236–1240, 1994.
Griffiths et al Infection & Immunity 47: 808–813, 1985.
Griffiths et al FEMS Microbiology Letters 16:95–99, 1983.
Ikeda et al Infection & Immunity 56:2499–2502, 1988.
Chant et al. Journal of General Microbiology 131:1503–1509, 1985.
Gilmour et al Vaccine 9:137–140, 1991.
Choi–Kim et al Vet. Microbiol 28:75–92, 1991.
Glisson et al Avian Disease 37:1074–1079, 1993.
Banerjee–Bhatnagar et al., "Expression of *Neisseria meningitidis* Iron–Regulated Outer Membrane Proteins, Including a 70–Kilodalton Transferrin Receptor, and Their Potential for Use as Vaccines", *Infect. Immunity*, 58, 2875–2881 (1990).
Boothby et al., "Characterization of Antigens from Mycoplasmas of Animal Origin", *Am. J. Vet. Res.*, 44, 433–439 (1983).
Brogden et al., "Lysates of Turkey–grown *Pasteurella multocida*: Effects of Solubilizing Agents on the Immunologic Properties of Membrane Vesicles", *Am. J. Vet. Res.*, 44, 428–432 (1983).
Crosa, "The Relationship of Plasmid–Mediated Iron Transport and Bacterial Virulence", *Ann. Rev. Microbiol.*, 38, 69–89 (1984).
El–Shobaki et al., "Mucosal Transferrin and Ferritin Factors in the Regulation of Iron Absorption", *Res. Exp. Med.*, 171, 243–253 (1977).
Filip et al., "Solubilization of the Cytoplasmic Membrane of *Escherichia coli* by the Ionic Detergent Sodium–Lauryl Sarcosinate", *J. Bacteriology*, 115, 717–722 (1973).
Finkelstein et al., "Role of Iron in Microbe–Host Interactions", *Rev. Infect. Diseases*, 5, S759–S777 (1983).
Furugouri, "Iron Binding Substances in the Intestinal Mucosa of Neonatal Piglets", *J. Nutr.*, 107, 487–494 (1977).
Gilleland, Jr. et al., "Perspectives on the Potential for Successful Development of Outer Membrane Protein Vaccines", *Eur. J. Clin. Microbiol.*, 6, 231–233 (1987).
Glisson et al., "In Vivo Antigen Expression by *Pasteurella multocida*", *Avian Diseases*, 35, 392–396 (1991).
Goding, *Monoclonal Antibodies: Principles and Practice*, Academic Press, 162–165 (1986).
Harlow et al., *Antibodies: A Laboratory Manual*, Cold Spring Harbor Laboratory, 689 (1988).
Lu et al., "A Monoclonal Antibody Against a *Pasteurella multocida* Outer Membrane Protein Protects Rabbits and Mice Against Pasteurellosis", *Infect. Immun.*, 59, 172–180 (1991).
Lu et al., "The Outer Membrane of *Pasteurella multocida* 3:A Protects Rabbits Against Homologous Challenge", *Infect. Immun.*, 59, 4517–4523 (1991).
Mazurier et al., "Visualization of Lactotransferrin Brush–Border Receptors by Ligand–Blotting", *Biochem. Biophys. Acta*, 821, 453–460 (1985).
Neilands, "Microbial Iron Compounds", *Ann. Rev. Biochem.*, 50, 715–731 (1981).
Ogawa et al., "Immunochemical and Biological Characterization of Outer Membrane Proteins of *Porphyromonas endodontalis*", *Infect. Immun.*, 60, 4528–4533 (1992).
Ogunnariwo et al., "Evidence for Non–Siderophore–Mediated Acquisition of Transferrin–Bound Iron by *Pasteurella multocida*", *Microbial Pathogenesis*, 11, 47–56 (1991).

(List continued on next page.)

*Primary Examiner*—Hazel F. Sidberry
*Attorney, Agent, or Firm*—Merchant, Gould, Smith, Edell, Welter & Schmidt, P.A.

[57] ABSTRACT

The invention provides a vaccine for immunizing poultry and other animals against infection by a gram-negative bacteria, and a method of immunizing an animal using the vaccine. The vaccine may contain purified siderophore receptor proteins derived from a single strain or species of gram-negative bacteria or other organism, which are cross-reactive with siderophores produced by two or more strains, species or genera of gram-negative bacteria. The invention further provides a process for isolating and purifying the siderophore receptor proteins, and for preparing a vaccine containing the proteins. Also provided is a method for diagnosing gram-negative sepsis.

16 Claims, 9 Drawing Sheets

OTHER PUBLICATIONS

Ogunnariwo et al., "Correlation Between the Ability of Haemophilus paragallinarum to Acquire Ovotransferrin–Bound Iron and the Expression of Ovotransferrin–Specific Receptors", *Avian Diseases*, 36, 655–663 (1992).

Rimler, "Cross–Protection Factor(s) of *Pasteurella multocida*: Passive Immunization of Turkeys Against Fowl Cholera Caused by Different Serotypes", *Avian Diseases*, 31, 884–887 (1987).

Rimler et al., "Solubilization of Membrane–Associated Cross–Protection Factor(s) of *Pasteurella multocida*", *Avian Diseases*, 35, 258–263 (1989).

Snipes et al., "Plasma– and Iron–regulated Expression of High Molecular Weight Outer Membrane Proteins by *Pasteurella multocida*", *Am. J. Vet. Res.*, 49, 1336–1338 (1988).

Stuart et al., "Iron–Suppressible Production of Hydroxamate by *Escherichia coli* Isolates", *Infect. Immun.*, 36, 870–875 (1982).

Truscott et al., "Demonstration of an Outer Membrane Protein with Antiphagocytic Activity from *Pasteurella multocida* of Avian Origin", *Infect. Immunity*, 56, 1538–1544 (1988).

Coulton et al., "Protein II Influences Ferrichrome–iron Transport in *Escherichia coli* K12", *J. Gen. Microbiol.*, 110, 211–220 (1979).

Crichton, *Inorganic Biochemistry of Iron Metabolism*, Ellis Horwood, 59–63, 234, 239 (1991).

Francis et al., "Immunological Priming with Synthetic Peptides of Foot–and–Mouth Disease Virus", *J. Gen. Virol.*, 66, 2347–2354 (1985).

Helenius et al., "Solubilization of Membranes by Detergents", *Biochim. Biophys. Acta*, 415, 29–79 (1975).

Hjelmeland, "Solubilization of Native Membrane Proteins", *Methods in Enzymology: Guide to Protein Purification*, Academic Press, 182, 253–264 (1990).

Hudson et al., *Practical Immunology*, Oxford, v, 58–59 (3d ed. 1989).

Jousimies et al., "Genetic Analysis of *Salmonella minnesota* R Mutants with Defects in the Biosynthesis of the Lipopolysaccharide Core", *J. of Bacteriology*, 119, 753–759 (1974).

Luderitz et al., "Lipopolysaccharides, the O anigens and endotoxins of Gram–negative bacteria: Relationships of chemical structure and biological activity", *The Virulence of Escherichia coli*, Sussman, ed., The Society for General Microbiology, Academic Press, 73–88 (1985).

Medearis, Jr. et al., "Cell Wall Composition and Virulence in *Escherichia Coli*", *The Journal of Experimental Medicine*, 128, 399–414 (1968).

Neugebauer, "Detergents: An Overview", *Methods in Enzymology: Guide to Protein Purification*, Academic Press, 182, 239–253 (1990).

Osborn et al., "Proteins of the Outer Membrane of Gram–Negative Bacteria", *Ann. Rev. Microbiol.*, 34, 369–422 (1980).

Overbeek et al., "Carumonam Enhances Reactivity of *Escherichia coli* with Mono– and Polyclonal Antisera to Rough Mutant *Escherichia coli* J5", *J. Clin Microbiol.*, 25, 1009–1013 (1987).

Sigma Chemical Co., *Product Catalogue: Biochemicals, Organic Compounds for Research and Diagnostic Reagents*, 1562–1567 (1993).

Danve et al., *Vaccine*, 11, 1214–1220, 1992.

Hirst et al., *Fish & Shellfish Immunology*, 4, 29–45, 1994 (Abstract only).

Nilius et al., *J. Med. Vet. Mycol.*, 28, 395–404, 1990 (Abstract only).

Viscar et al., *FEMS Microbiology*, 79, 225–232, 1991.

Makela et al., *J. Bacteriol.* 119:760–764 (1974).

ACTIVE IMMUNIZATION USING A SIDEROPHORE RECEPTOR PROTEIN

CROSS REFERENCE TO RELATED APPLICATIONS

This patent application is a continuation-in-part of U.S. patent application Ser. No. 08/194,040, filed Feb. 9, 1994 now abandoned.

BACKGROUND OF INVENTION

The economic impact of infectious diseases in the poultry industry is well-appreciated. Immunization of birds has helped reduce the cost of production by decreasing the incidence of gastrointestinal, respiratory and systemic diseases. While vaccines provide adequate immunity for those pathogens against which a flock has been immunized, there are few vaccines which can provide broad-based cross-protection against unanticipated diseases or against those diseases for which an animal has not been specifically vaccinated.

A number of important diseases of domestic poultry are caused by bacteria able to invade host tissues, such as *Salmonella spp., Escherichia spp.* and *Pasteurella spp.* While many vaccines are available for immunization against individual species and serotypes, none provide cross-protection or stimulate broad-based immunity against multiple serotypes, species or genera.

One essential factor required for a bacteria to induce clinical disease is the ability to proliferate successfully in a host tissue. Iron is an essential nutrient for the growth of gram-negative bacteria in vivo, but is virtually unavailable in mammalian and/or avian tissues because the iron is either intracellular or extracellular, complexed with high affinity, iron-binding proteins, for example, transferring in blood and lymph fluids and lactoferrin in external secretions. In normal tissues, the concentration of iron is approximately $10^{-18}$M, far below that required for bacterial growth.

To circumvent these restrictive conditions, pathogenic bacteria have evolved high affinity iron transport systems produced under low iron conditions, which consist of specific ferric iron chelaters, "siderophores," and iron-regulated outer membrane proteins (IROMPs) and/or siderophore receptor proteins (SRPs) which are receptors for siderophores on the outer membrane of the bacterial cell. Siderophores are synthesized by and secreted from the cells of gram-negative bacteria under conditions of low iron. Siderophores are low molecular weight proteins ranging in molecular mass from about 500 to about 1000 MW, which chelate ferric iron and then bind to IROMPs in the outer bacterial membrane which, in turn, transport the iron into the bacterial cell. Although the use of IROMPs as immunogens has been considered, these proteins have not been examined for such use, at least in part, due to an inability to extract these proteins from bacterial membranes in high volume and with a desired level of purity and immunogenic quality.

Accordingly, an object of the invention is to provide a method for obtaining high amounts of immunogenic quality siderophore receptor proteins from *Escherichia coli*, Salmonella, Pasteurella, and other gram-negative bacteria. Another object is to provide a vaccine for immunizing poultry and other animals against these bacteria. Yet another object is to provide a vaccine for cross-protection against multiple serotypes, species and/or genera of bacteria belonging to the family Enterobacteriaceae and/or Pasteurellaceae. A further object is to provide a diagnostic assay to monitor and/or profile sepsis and subclinical disease caused by gram-negative bacteria under field conditions.

SUMMARY OF THE INVENTION

These and other objects are achieved by the present invention which is directed to a vaccine for prevention and treatment of infection by gram-negative bacteria, and a method of immunizing poultry and other animals against such infections using the vaccine. The invention also provides a method for isolating and purifying outer membrane siderophore receptor proteins from gram-negative bacteria for producing the vaccine. The invention further provides an in vitro method of diagnosing infections of gram-negative bacteria in an animal using antibodies raised to the isolated receptor proteins.

The vaccine is useful for immunizing an avian or other animal against infection by gram-negative bacteria such as colibacillosis, salmonellosis and pasteurellosis. The vaccine is composed of a substantially pure siderophore receptor protein derived from the outer membrane of a gram-negative bacteria, for example, *Salmonella spp., Escherichia spp.* and *Pasteurella spp*. A siderophore receptor protein, useful according to the invention, is a protein or antigenic peptide sequence thereof derived from the outer membrane of a gram negative bacterium, which is capable of producing an antibody that will react with the siderophore receptor protein expressed by a gram-negative bacteria of the same or different strain, species or genus. Preferably, the siderophore receptor protein is derived from a bacterium belonging to the family Enterobacteriaceae and/or Pasteurellaceae.

The vaccine contains siderophore receptor proteins (SRPs) derived from a gram-negative bacteria, capable of eliciting an immune response in an animal with the production of anti-SRP antibodies. These antibodies will react with siderophore receptor proteins of that bacteria, and may also cross-react with siderophore receptor proteins of a different strain, species and/or genera of gram-negative bacteria to provide cross-protection against infection from such other bacteria. Useful siderophore receptor proteins having a molecular weight of about 72–96 kDa, as determined by SDS-PAGE, have been isolated from *E. coli, Salmonella spp., Pasteurella spp., Pseudomonas spp.*, and *Klebsiella spp*. Preferably, the siderophore receptor proteins (SRPS) are derived from *Escherichia coli, Salmonella spp.* and/or *Pasteurella spp*. The antibodies produced from those SRPs will react with SRPs of those bacteria and cross-react with SRPs of a different strain, species and/or genera of bacteria within the family Enterobacteriaceae and/or Pasteurellaceae.

The vaccine contains one or more siderophore receptor proteins extracted from the outer membrane of a single strain or species, or two or more different strains or species of gram-negative bacteria. The amount and type of siderophore receptor protein included in the vaccine is effective to stimulate production of antibodies reactive with a siderophore receptor protein of one, preferably two or more strains, species or genera of gram-negative bacteria. A preferred vaccine is composed of an amount and profile of siderophore receptor proteins to effectively induce antibodies reactive with a majority, preferably all, of the siderophore receptor proteins of a bacterial population to effectively enhance opsonization and complement-mediated bacterial lysis, and/or block the iron binding capacity of the bacteria. The siderophore receptor protein is combined with a physiologically-acceptable carrier, preferably a liquid. The vaccine may further include an adjuvant to enhance the immune response, and other additives as desired, such as preservatives, flavoring agents, buffering agents, and the like.

The present invention also provides a method for isolating high quantities of immunogenically effective siderophore receptor proteins from outer membranes of a single strain or species of gram-negative bacteria such as E. coli, Salmonella and/or Pasteurella. The method includes culturing the organism under conditions of low iron availability, that is, in a culture medium that lacks iron or includes an iron chelating agent. The siderophore receptor proteins are then separated from the bacterial outer membrane and purified by use of the anionic detergent, sodium dodecyl sulfate, preferably under non-reducing conditions.

The siderophore receptor proteins may be utilized to raise polyclonal antibody sera and monoclonal antibodies for use in passive immunization therapies. Such antibodies may also be used in an in vitro method of diagnosing a gram-negative bacterial infection in an animal. The diagnostic method includes contacting a body material potentially infected with a gram-negative bacteria, such as a tissue sample or body fluid, with a labelled antibody raised to a siderophore receptor protein, and detecting the label in the complex formed between the siderophore receptor protein in the body material and the labelled antibody. The method may also be performed by combining the body sample with the antibody to the siderophore receptor protein, and then contacting the sample with a labelled anti-species antibody reactive with the protein-specific antibody, and then detecting the label.

The siderophore receptor proteins car also be used as capture antigens in a method of monitoring and profiling gram negative sepsis. For example, the protein may be used in an ELISA technique in which the protein is bound to a solid support and contacted with a sample material to react with and detect antibodies present in the sample.

DETAILED DESCRIPTION OF THE INVENTION

Figure 1:
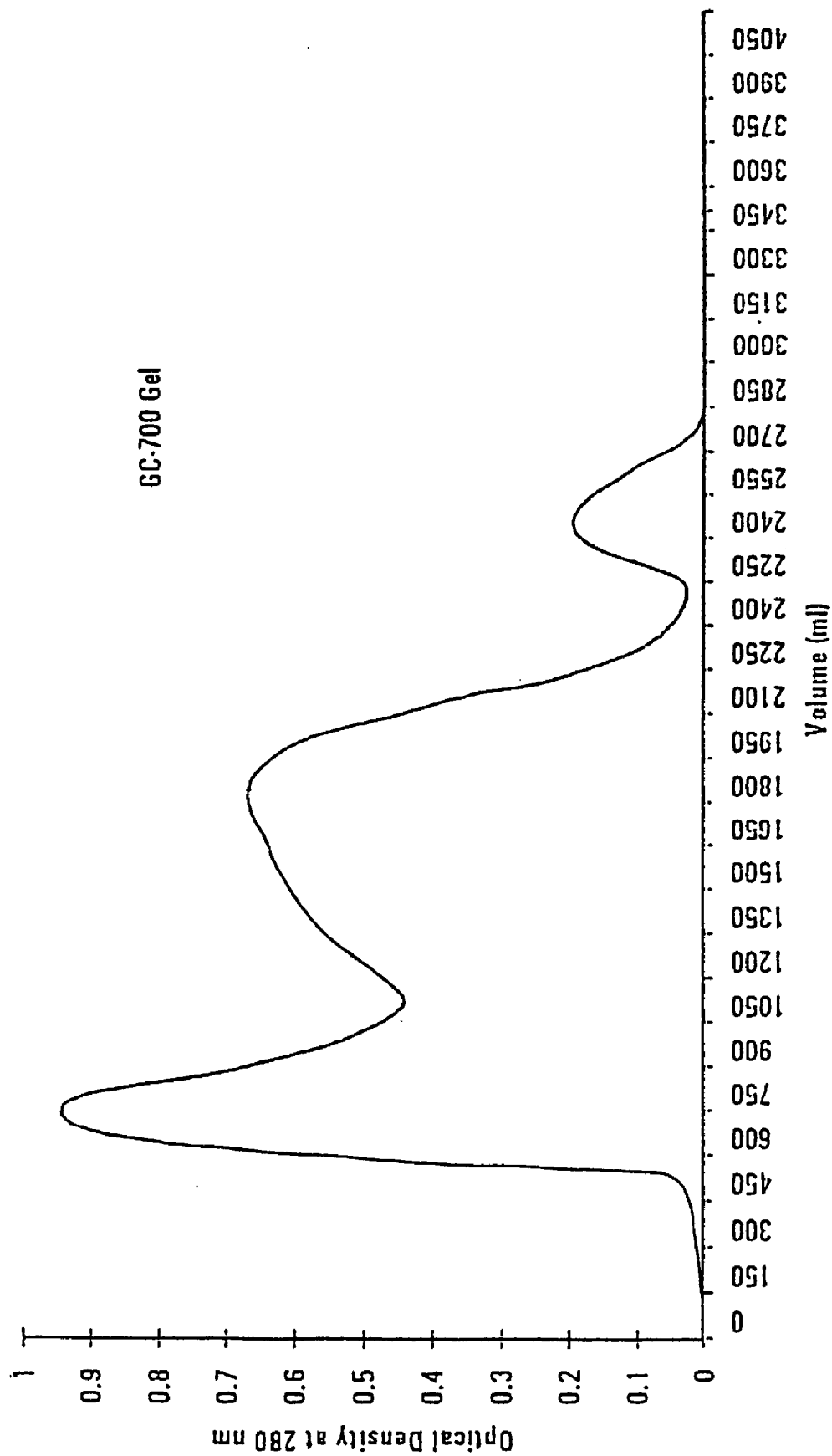
FIG. 1 is a graphic depiction of the elution profile of concentrated, solubilized siderophore receptor proteins isolated from *Escherichia coli* serotype 078 (ATCC 55652).
Figure 2:
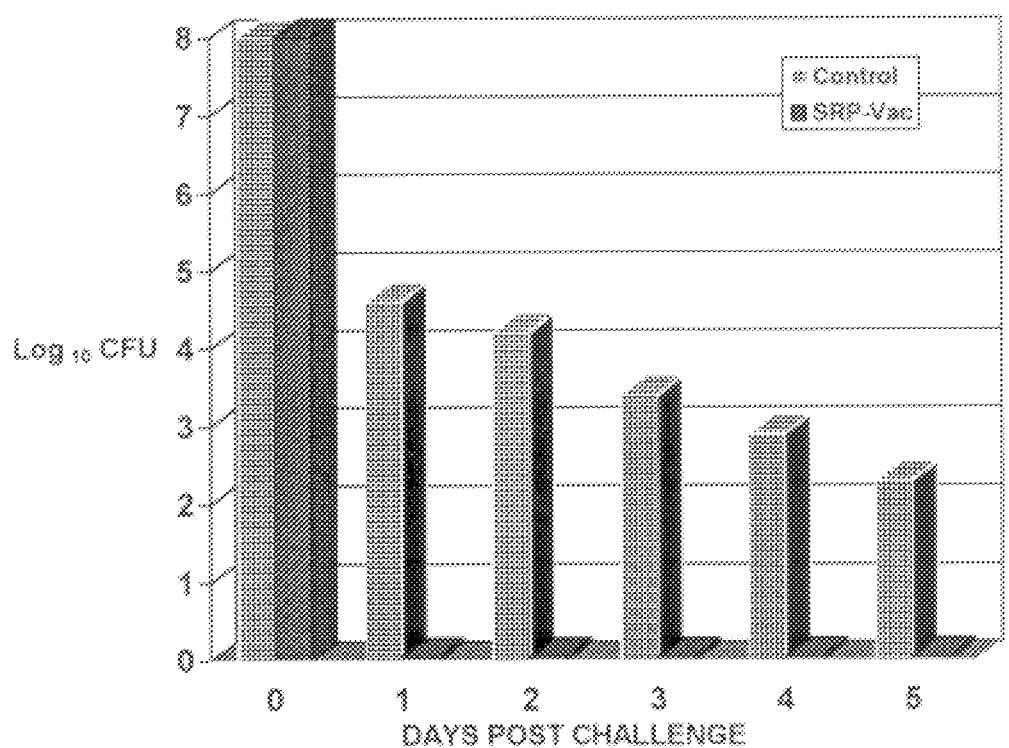
FIG. 2 is a graphic depiction of the quantitative clearance of *Salmonella agona* in spleens of turkeys vaccinated with IROMPs isolated from *E. coli* and non-vaccinated controls.

As used herein, the term "substantially pure" means that the siderophore receptor protein has been extracted and isolated from its natural association with other proteins, lipids, and other like substances and elements of a bacterial cell or other organism.

Gram-negative bacteria are frequent pathogens of poultry and other animals, such as domestic foul, livestock, horses, companion animals, and humans. In an iron-restricted environment, bacteria such as *Escherichia coli, Salmonella spp.* and *Pasteurella spp.* produce siderophores that chelate ferric iron and bind to outer membrane proteins that function as siderophore receptors on the bacterial membrane.

The invention provides an improved process for isolating and separating siderophore receptor proteins from the outer membrane of gram-negative bacteria. Isolation and purification of immunogenically intact siderophore receptor proteins from bacterial membranes in a sufficient quantity and immunogenic quality for formulating a vaccine against infection by gram-negative bacteria has been difficult. The structural orientation, or conformation, of the outer membrane protein necessary to provide antigenicity may be typically lost when the protein is separated and purified from the lipopolysaccharide complex. Another problem is that the protein becomes denatured by the separation process wherein its immunogenicity is lost. According to the present invention, however, the isolation and separation of immunogenic quantities of antigenically effective siderophore receptor proteins from the outer membrane of gram-negative bacteria has been achieved. This enables the production of vaccines and hyperimmunized sera for the treatment of animals infected or susceptible to infection by gram-negative bacteria, and in vitro diagnostic methods for detecting such an infection in an animal.

As a group, gram-negative bacteria possess a common cell wall structure. Components of the cell wall structure may be used as immunogens. However, these immunogens may provide only homologous immune protection. The present vaccine utilizes a combination of outer membrane siderophore receptor proteins common to two or more gram-negative bacteria that are capable of proliferating in the blood or host tissues and causing infection in an animal. The vaccine may contain two or more siderophore receptor proteins (SRPs), preferably four or more SRPs derived from the outer membrane of one or more strains or species of gram-negative bacteria and/or other organism. Preferably, the SRPs are derived from a single strain or species of gram-negative bacteria. A preferred siderophore receptor protein for use in the vaccine has a common receptor reactive with siderophores produced by two or more strains, species and/or genera of gram-negative bacteria.

An example of a useful siderophore receptor protein is the receptor protein for aerobactin (MW about 72–74 kDa) produced by members of the family Enterobacteriaceae, for example, *Escherichia coli*, Salmonella and Klebsiella. Antibodies produced against an aerobactin receptor protein of one species, strain or genus of that family have been found to cross-react with other bacteria within the family. Species of Pseudomonas of the family Pseudomonadaceae also express aerobactin siderophore receptor proteins that can be isolated according to the invention and used in a vaccine to produce antibodies that cross-react with the aerobactin receptor proteins of *E. coli*, Salmonella and Klebsiella, among other members of the family Enterobacteriaceae.

Another example of a suitable siderophore receptor protein for use in the present vaccines is that produced by *Pasteurella multocida* for the siderophore multocidin (MW about 500–1000 kDa). Antibodies to the multocidin receptor protein will react with all three of the SRPs in *Pasteurella multocida*. In Western blots, two of the larger siderophore proteins (96 kDa, 84 kDa) of *P. multocida* showed reactivity with hyperimmune *E. coli* protein antisera. Antibodies produced to multocidin receptor proteins will cross-react with the siderophore receptor proteins of *Salmonella spp.* and *E. coli*, as demonstrated by ELISA and Western blot analysis.

Other siderophore receptor proteins include those reactive with the siderophore enterochelin (MW about 81–84 kDa) produced by *E. coli*, Salmonella, Pseudomonas and Klebsiella; and the siderophore citrate (MW about 74–78 kDa) produced by *E. coli*, among others. A vaccine containing the enterochelin and/or citrate receptor proteins will produce antibodies reactive with *E. coli*, Salmonella and other bacteria of the family Enterobacteriaceae, and with Pseudomonas of the family Pseudomonadaceae.

Another useful SRP is the siderophore receptor protein for ferrichrome (MW about 78 kDa) produced by *E. coli*, and *Salmonella spp*. In commercial poultry raising facilities, infection by Aspergillus causes serious respiratory problems in the birds. In the lungs, Aspergillus will excrete ferrichrome to acquire iron as a growth nutrient. Under iron restriction or systemic conditions, *E. coli* and Salmonella will express ferrichrome receptor protein. They are also opportunistic bacteria that can scavenge and utilize ferrichrome produced by Aspergillus as a growth nutrient. Therefore, it is preferred that the vaccine preparation include a ferrichrome receptor protein to induce antibodies that will bind and cross-react with the ferrichrome receptor proteins of gram-negative bacteria including *E. coli* and Salmonella, and fungi/mold. A vaccine containing this SRP will elicit an immune response to the protein to enhance the bactericidal activity of the antibody. Also, once the avian or other animal is vaccinated with a ferrichrome receptor protein, Aspergillus expressing this protein in vivo in the animal will enhance the antibody response to the ferrichrome receptor protein which in turn will cross-react with Salmonella and *E. coli* and other bacteria that express the ferrichrome receptor protein.

Antibody elicited from a ferrichrome receptor protein (MW about 78 kDa) derived from *E. coli* can cross-react with the receptor proteins of fungi, such as *Aspergillus flavus, Aspergillus fumigatus*, Penicillium and Fusarium. Western blot analysis against the outer membrane proteins (OMPs) of *A. fumigatus* using anti-SRP antibody revealed three cross-reactive proteins (MW about 45–90 kDa). The inclusion of a ferrichrome receptor protein into a vaccine preparation will provide inducement of antibodies that will react with the fungi and/or bacteria to prevent binding and excretion of the ferrichrome siderophore. Animals such as birds that are vaccinated with a vaccine preparation containing a ferrichrome receptor protein will get an elevated antibody titer by bacteria and/or fungi that challenge the animal and produce a ferrichrome receptor protein. Also, antibody to the ferrichrome receptor can be elevated by natural field challenge by bacteria or fungi which can induce a bactericidal effect that could lessen system challenge and disease potential.

Yet another useful SRP is a coprogen receptor protein (MW about 74–76 kDa) produced by *E. coli*. Antibodies produced against coprogen receptor protein will cross-react with the SRPs of other *E. coli* expressing this protein under systemic conditions.

In one embodiment, the vaccine is formulated with siderophore receptor proteins (SRPs) of different types and/or molecular weights, derived from a first gram-negative bacteria, the SRPs being capable of stimulating production of antibodies that react with the first gram-negative bacteria as well as a second gram-negative bacteria of a different strain or species than the first gram-negative bacteria. The vaccine preferably contains all SRPs derived from the gram-negative bacteria infectious agent. For example, *P. multocida* and *Salmonella spp*. have been identified as producing 3 SRPs each, and *E. coli* produced 2, 3, 4, and 6 SRPs varying between serotypes. Accordingly, the vaccine is formulated to contain the SRPs derived from the bacterial causative agent, i.e., 2–6 or more SRPs. It is preferred that the vaccine also include siderophore receptor proteins of different types and/or molecular weights derived from a gram-negative bacteria of a strain or species different than the first gram-negative bacteria, preferably 1–15 SRPs, preferably 5–10 SRPs.

For example, the vaccine may contain a siderophore receptor protein derived from *E. coli*, preferably *E. coli* serotype 01a, 02a and/or 078, that is capable of stimulating production of an antibody immunoreactive with that *E. coli* and a second gram-negative bacteria such as *Salmonella spp., Pseudomonas aeruginosa, Klebsiella pneumoniae* and/or *Pasteurella multocida*. In another example, the vaccine may contain a siderophore receptor protein derived from a species of Pasteurella, such as *P. multocida*, that is capable of stimulating production of an antibody immunoreactive with that species of Pasteurella and a second gram-negative bacteria such as *Salmonella spp*. and/or *E. coli*. In yet another example, the vaccine may contain a siderophore receptor protein derived from a species of Salmonella that is capable of stimulating production of an antibody immunoreactive with that species of that species of Salmonella, and a second gram-negative bacteria such as *E. coli*, Pseudomonas, Klebsiella, and/or *Pasteurella multocida*.

A vaccine formulated with siderophore receptor proteins derived from *E. coli* is preferably composed of an aerobactin, ferrichrome, coprogen, enterochelin and/or citrate SRP, having molecular weights of about 89 kDa to about 72 kDa, as determined by SDS-PAGE. The vaccine preferably includes 2–5 receptor proteins, preferably 3–5 proteins, preferably all five *E. coli* SRPs. A preferred vaccine against *E. coli* infection is prepared with the SRPs from *E. coli* 078 (ATCC #55652). *E. coli* 078 has been identified as producing up to 6 SRPs ranging in molecular weight from about 72 to 90 to 92 kDa, as determined by SDS-PAGE. The SRPs derived from *E. coli* 078 include aerobactin, ferrichrome, coprogen, enterochelin and citrate SRPs, having molecular weights of about 91–92 kDa, 89 kDa, 84 kDa, 78 kDa, 74 kDa and 72 kDa, as determined by SDS-PAGE, 12.5% acrylamide reducing gel. Although the 91–92 kDa proteins of *E. coli* O78 are expressed in culture media made with and without iron, the expression of those proteins is enhanced in an iron-restricted medium, and as used herein, the 91–92 kDa proteins are considered to be iron-regulated SRPs. A preferred vaccine for immunizing an animal against *E. coli* is formulated with an aerobactin, ferrichrome, coprogen, enterochelin and citrate SRP derived from *E. coli*, preferably *E. coli* O78, made of at least 5 siderophore receptor proteins, preferably at least 6 receptor proteins, or more, to induce anti-SRP antibodies to effectively block a majority, preferably all, iron binding sites of *E. coli* serotypes present in an infection, and to induce high antibody levels to promote bactericidal activity.

It is further preferred that the vaccine includes one or more SRPs, preferably about 1–15 SRPs, derived from one or more additional bacteria, different from the first gram-negative bacteria. For example, in a vaccine composed of SRPs from *E. coli*, it is desirable to include one or more of the SRPs derived from Salmonella, *Pasteurella multocida*, Klebsiella and/or Pseudomonas.

A preferred vaccine contains each of the SRPs of different types and/or molecular weights, of a population of gram-negative bacteria to induce production of antibodies that will effectively block the iron-binding sites of all of the various SRPs of the bacterial population so that the bacteria cannot effectively bind iron as a nutrient for growth. It is also preferred that the vaccine will induce high SRP antibody levels that will enhance opsonization and/or complement-mediated bacterial lysis. Due to the variation in iron-regulated outer membrane proteins (IROMPs) produced between and within bacterial serotypes, formulating a vaccine with SRPs isolated and purified from a single isolate source may provide only a partial profile of the SRPs present in a bacterial population. Consequently, the effectiveness of the vaccine to induce anti-SRP antibodies to block bacterial iron-binding sites and inhibit bacterial infection may be limited to those serotypes that produce all or less than all of the SRPs included in the vaccine, while those bacterial serotypes producing other SRPs may retain an iron-binding capacity. Thus, it is preferred that a profile, or banding pattern (i.e., SDS-PAGE protein separations), of a bacterial population is conducted by examining different field isolates, preferably about 25–100 isolates, to determine the SRPs that are present, and all of the various SRPs are included in the vaccine.

Non-iron regulated proteins and polypeptides may also be included in the vaccine as adjuvants to enhance the effectiveness of the vaccine and increase opsonization, that is, increase macrophage activity resulting in increased phagocytosis of antibody-bound cells, and induce complement-mediated bacterial lysis. A useful adjuvant protein is a 34–38 kDa group of outer membrane proteins (porins, i.e., pore-forming proteins) derived from gram-negative bacteria of the family Enterobacteriaceae and Pasteurellaceae including *E. coli* O78, and other gram-negative bacteria. The transmembrane and porin proteins (MW 34–38 kDa) identified as OmpA, OmpC, OmpD and OmpF are expressed with and without iron, are relatively conserved between gram-negative bacteria, and play a role in iron binding. For example, OmpF and OmpC will bind lactoferrin (Erdei et al., *Infection and Immunity* 62:1236–1240 (April 1994)), while OmpA will bind ferrichrome (Coulton et al., *J. Gen. Microbiol.* 110:211–220 (1979)). Antibodies early in infection particularly of the IgM class will cross-react with outer membrane proteins of *E. coli*, Salmonella, Pasteurella, Pseudomonas and Klebsiella, and will bind lactoferrin and/or ferrichrome, precluding the availability of an iron source for bacterial growth. Antibodies to these proteins will also bind to the porin Omp on the surface to enhance opsonization and/or complement-mediated bacterial lysis. Immunogenically intact 34–38 kDa porin outer membrane proteins can be isolated and purified according to the process of the invention.

The vaccine may be used to immunize poultry and other animals such as domestic fowl, livestock, horses, companion animals, and humans, against infection caused by one or more gram-negative bacteria. The vaccine is effective for eliciting antibodies that are immunoreactive with a gram-negative bacteria that expresses one or more siderophore receptor protein(s).

Preferably, the vaccine is capable of achieving clinical efficacy of cross-reactive and cross-protective immunization against two or more different strains, species and/or genera of gram-negative bacteria or other organisms capable of expressing siderophore receptor proteins. For example, a vaccine containing siderophore receptor proteins for aerobactin, enterochelin, ferrichrome, coprogen and/or citrate, may be used to stimulate production of antibodies that cross-react with a number of different bacteria that express one or more of these receptor proteins. The effectiveness of the present vaccine is due, at least in part, to the conservative nature of the outer membrane siderophore receptor proteins which are cross-reactive with siderophore receptor proteins produced by two or more different species, strains and/or genera of Enterobacteriaceae such as *E. coli*, Salmonella, and other gram-negative bacteria within other families such as Pasteurella and/or Pseudomonas.

Because of the cross-reactivity of the SRPs, the vaccine is effective in stimulating production of antibodies that react with the first gram-negative bacteria (from which the SRPs were derived), as well as a second gram-negative bacteria of a different strain or species than the first gram-negative bacteria. For example, a vaccine can be formulated to contain a siderophore receptor protein derived from *E. coli*, preferably *E. coli* serotype O1a, O2a and/or O78, more preferably *E. coli* O78, that is effective in stimulating production in vivo of an antibody immunoreactive with that *E. coli* serotype (from which the SRP(s) were derived), and a second gram-negative bacteria such as *Salmonella spp., Pseudomonas aeruginosa, Klebsiella pneumoniae* and/or *Pasteurella multocida*. In another example, the vaccine can contain a siderophore receptor protein derived from a species of Pasteurella, such as *P. multocida*, that is effective in stimulating production of an antibody immunoreactive with that species of Pasteurella and a second gram-negative bacteria such as *Salmonella spp.* and/or *E. coli*. In yet another example, the vaccine can contain a siderophore receptor protein derived from a species of Salmonella that is effective in stimulating production of an antibody immunoreactive with that species of Salmonella, and a second gram-negative bacteria such as *E. coli*, Pseudomonas, Klebsiella, and/or *Pasteurella multocida*.

Advantageously, immunization using the present vaccine containing an immunogen cross-reactive with multiple species, strains and genera of gram-negative bacteria, not only minimizes immunization costs since separate inoculations with a different immunogen for each type of gram-negative bacteria is not required. In addition, the present vaccine provides protection against new strains or unanticipated pathogens of gram-negative bacteria which produce siderophore receptor proteins that will cross react with antibodies induced by the siderophore receptor proteins contained in the vaccine. The vaccine given to an adult animal is highly efficacious in treating and preventing gram-negative sepsis not only in the adult animal but also their progeny by the direct transfer of anti-SRP antibodies.

Commercial bacterial whole cell vaccines are useful for treating a particular disease and/or infection but do not provide effective cross-protection against other infection. For example, avian pasteurellosis in turkeys caused by *Pasteurella multocida* is clinically diagnosed by particular lesions induced by the bacterial infection. Treating the disease with a commercial whole cell vaccine stimulates antibodies that are homologous but not heterologous in their action, and will not cross-protect against infection by other bacteria.

Advantageously, the present vaccines provide cross-protection against a number of infections caused by gram-negative bacteria. According to the invention, an animal species suffering from gram-negative bacterial sepsis can be administered the vaccine containing SRPs derived from the (causative agent) gram-negative bacteria to induce antibodies immunoreactive with those SRP(s) to inhibit the disease state. The antibodies will also cross-react with SRP(s) produced by another gram-negative bacteria to inhibit a disease state caused by that other bacteria. Thus, a vaccine containing SRPs of a first gram-negative bacteria will provide protection against an infection caused by that bacteria and provide cross-protection against infection caused by a different gram-negative bacteria.

Gram-negative bacteria suitable for use in obtaining siderophore receptor proteins according to the invention, are those capable of producing siderophore receptor proteins when raised under growth conditions of low iron availability. Examples of useful gram-negative bacteria include *Escherichia coli* (serotypes 01a, 02a, and 078), *Salmonella agona, Salmonella blockley, Salmonella enteriditis, Salmonella hadar, Salmonella heidelberg, Salmonella montevideo, Salmonella senftenberg, Salmonella cholerasuis, Salmonella typhimurium, Pasteurella multocida* (serotype A:3,4), *Klebsiella pneumoniae, Pseudomonas aeruginosa*, and the like. These organisms are commercially available from a depository such as American Type Culture Collection (ATCC), Rockville, Md. In addition, such organisms are readily obtainable by isolation techniques known and used in the art. The gram-negative bacteria may be derived from an infected animal as a field isolate, and screened for production of SRPs, and introduced directly into the preferred iron-depleted media for that bacteria, or stored for future use, for example, in a frozen repository at about −20° C. to about −95° C., preferably about −40° C. to about −50° C., in BHI containing 20% glycerol, and other like media.

For producing the siderophore receptor proteins, conditions of low iron availability are created using culture media that lack iron or have been supplemented with an iron chelating agent to decrease iron availability. Suitable culture media for providing low iron availability and promoting production of the siderophore receptor proteins in gram-negative bacteria, include media such as tryptic soy broth (Difco Laboratories, Detroit, Mich.) and/or brain-heart infusion (BHI) broth which has been combined with an iron-chelating agent, for example, α,α'-dipyridyl, deferoxamine, and other like agents. In a preferred embodiment, α,α-dipyridyl is added to a BHI culture media in a concentration of about 1–500 μg/ml, preferably about 50–250 μg/ml, more preferably about 75–150 μg/ml.

The gram-negative bacteria employed to produce a siderophore receptor protein are cultured in the preferred media for that organism using methodologies and apparati known and used in the art, such as a fermenter, gyrator shaker, or other like apparatus. For example, a culture may be grown in a gyrator shaker in which the media is stirred continuously with aeration at about 300–600 rev/minute, for about 15–20 hours, at a temperature and pH appropriate for growth for that organism, i.e., about 35°–45° C. and about pH 7–7.6, preferably pH 6.5–7.5. The bacterial culture is then processed to separate and purify the siderophore receptor proteins from the outer membrane of the bacteria.

The bacterial culture is concentrated, for example, by centrifugation, membrane concentration, and the like. For example, the cell culture may be centrifuged at about 2,450–20,000×g, preferably at about 5,000–16,000×g, for about 5–15 minutes at about 3°–6° C. The supernatant is removed by decanting, suctioning, pipetting and the like, and the concentrated cell pellet is collected and washed in a compatible buffer solution maintained at about pH 7–7.6, such as tris-buffered saline (TBS), N-2-hydroxyethylpiperazine-N'-2-ethanesulfonic acid (HEPES), 3-N(N-morpholino) propanesulfonic acid (MOPS), and the like. The washed pellet is resuspended and washed in a compatible buffer solution, i.e., TBS, HEPES, MOPS and the like. The cell material is then treated to solubilize the components of the outer membrane by resuspending the pellet in buffer containing about 0.5–10% sodium N-lauroyl sarcosinate, preferably about 1–3%, at about 4°–10° C. for about 15 minutes to about 3 hours, preferably about 30 minutes to about 2 hours, preferably with continuous stirring.

The bacterial cells are then disrupted by sonication, French pressure, grinding with abrasives, glass bead vortexing, and other like methods known and used in the art, preferably at a temperature of about 3°–6° C. The cell homogenate is then centrifuged at about 10,000–20,000×g for about 10–45 minutes, to separate cell debris from the supernatant fraction containing the outer membrane proteins. The supernatant is collected by decanting, suctioning, pipetting, or other like method, and then concentrated, for example, by ethanol precipitation, membrane concentration, propylene glycol precipitation, and other methods known and used in the art. In a preferred method, the supernatant is treated by passing it through a membrane having a molecular weight cut-off of about 1,000–50,000 MW, preferably about 10,000–25,000 MW, to concentrate the protein and allow contaminating proteins smaller than the molecular weight cut-off to pass through the membrane, and to decrease the amount of detergent. Such membranes are commercially available, for example, from Amicon, Danvers, Mass.

The concentrated supernatant is then reconstituted in a compatible buffer, i.e., TBS, HEPES, MOPS, and the like, about pH 7–7.6, which contains a detergent for solubilizing the outer membrane and extracting the siderophore receptor proteins. It was found that the anionic detergent sodium dodecyl sulfate (SDS), when used as a solubilizing detergent alone without a reducing agent such as 2-mercaptoethanol, is particularly effective for extracting a high quantity of the siderophore receptor proteins without denaturing or altering their immunogenicity such that the proteins will function in vivo as effective immunogens to elicit an antibody response against gram-negative bacteria. The buffer solution contains about 0.1–4% SDS (0.2%), preferably about 0.1–2% SDS, preferably about 0.1–2% SDS.

After about 1–10 minutes, the siderophore receptor proteins are separated from the buffer solution by affinity, ion exchange, size exclusion and other like chromatographic methods known and used in the art. Preferably, the SRP preparation is separated with a 4% stacking gel on a 12.5% acrylamide reducing gel. The fractions are then combined, concentrated, for example by centrifuging, and precipitated, for example with an alcohol (i.e., ethanol, methanol, acetone), to remove the SDS. The purified proteins may be used immediately to prepare a vaccine, or may be stored for future use through lyophilization, cryopreservation, or other like technique known and used in the art.

The vaccine of the present invention may be used for preventing and eliminating infections of gram-negative bacteria in poultry and other animals, including humans. The vaccine may be delivered to the animal, for example, by parenteral delivery, injection (subcutaneous or intramuscular), sustained-released repository, aerosolization, egg inoculation (i.e., poultry), and the like, by known techniques in the art. For prophylactic and anti-infectious therapeutic use in vivo, the vaccine contains an amount of a siderophore receptor protein to stimulate a level of active immunity in the animal to inhibit and/or eliminate gram-negative bacterial pathogenesis and/or sepsis.

The siderophore receptor proteins are administered in combination with a pharmaceutical carrier compatible with the protein and the animal. Suitable pharmacological carriers include, for example, physiological saline (0.85%), phosphate-buffered saline (PBS), Tris(hydroxymethyl aminomethane (TRIS), Tris-buffered saline, and the like. The protein may also be incorporated into a carrier which is a biocompatible and can incorporate the protein and provide for its controlled release or delivery, for example, a sustained release polymer such as a hydrogel, acrylate, polylactide, polycaprolactone, polyglycolide, or copolymer thereof. An example of a solid matrix for implantation into the animal and sustained release of the protein antigen into the body is a metabolizable matrix, as described, for example, in U.S. Pat. No. 4,452,775 (Kent), the disclosure of which is incorporated by reference herein.

Adjuvants may be included in the vaccine to enhance the immune response in the animal. Such adjuvants include, for example, aluminum hydroxide, aluminum phosphate, Freund's Incomplete Adjuvant (FCA), liposomes, ISCOM, and the like. The vaccine may also include additives such as buffers and preservatives to maintain isotonicity, physiological pH and stability. Parenteral and intravenous formulations of the vaccine may include an emulsifying and/or suspending agent, together with pharmaceutically-acceptable diluents to control the delivery and the dose amount of the vaccine.

Factors bearing on the vaccine dosage include, for example, the age and weight of the animal. The range of a given dose is about 25–5000 μg of the purified siderophore receptor protein per ml, preferably about 100–1000 μg/ml preferably given in about 0.1–5 ml doses. The vaccine should be administered to the animal in an amount effective to ensure that the animal will develop an immunity to protect against a gram-negative bacterial infection. For example, for poultry, a single dose of a vaccine made with Freund's Incomplete Adjuvant would contain about 150–300 μg of the purified siderophore receptor protein per ml. For immunizing a one-day of age bird of about 60 grams weight, the bird may be subcutaneously or intramuscularly injected with an about 0.25–0.5 ml dose. For an about 3-week old bird of about 1.5 lbs, the bird may be injected with about 0.25–1 ml dose. A vaccine for immunizing an about 5-lb. piglet against *Salmonella cholerasuis* would contain about 100–5000 μg protein per ml, preferably given in 1–5 ml doses. In each case, the immunizing dose would then be followed by a booster given at about 21–28 days after the first injection. Preferably, the vaccine is formulated with an amount of the siderophore receptor protein effective for immunizing a susceptible animal against an infection by two or more strains or species of gram-negative bacteria that express a siderophore receptor protein.

For boosting the immunizing dose, the booster may be a preparation of whole cells as conventionally used, or a chemically modified cell preparation, among others. For example, a useful booster is a preparation of a modified *E. coli* such as avirulent R-mutants, as for example, *E. coli* J5 (commercially available from ATCC as ATCC #43754; described by Overbeek et al., *J. Clin. Microbiol.* 25:1009–1013 (1987)), or *Salmonella minnesota* (commercially available from ATCC as ATCC #49284; as described by Jousimies et al., *J. Bacteriol.* 119:753–759 (1974), and Makela et al., *J. Bacteriol.* 119:760–764 (1974)) that lack outer oligosaccharide side chains of the lipopolysaccharide (LPS) layer of the outer membrane. Outer oligosaccharide side chains tend to mask SRPs on the cell membrane in such a way that the immune system does not recognize the SRPs and anti-SRP antibody titers are depressed. To enhance the ability of a booster made with intact bacterial cells to elicit an anti-SRP immune response, the cell membrane of the bacteria can be chemically altered to eliminate the interfering oligosaccharide side chains. Boosting with chemically-modified bacteria such as an R-mutant, advantageously provides an anti-SRP antibody titer that is 5–20 times higher than booster made of a non-modified whole cell bacterial preparation, or a natural field challenge.

Although not intended as a limitation of the invention, the mechanism by which immunization with the present vaccine provides protection against gram-negative bacterial infection is believed to be as follows. After an animal has been immunized with the vaccine, upon being challenged with a pathogenic strain of gram-negative bacteria, the body responds by producing humoral antibodies that block the siderophore receptor proteins on the outer membrane of the bacteria. This prevents iron uptake by the cell, which, in turn, eventually starves the bacteria of required iron nutrients. Another mechanism is that humoral antibodies produced in response to the siderophore receptor proteins in the vaccine, bind to the siderophore receptor protein on the bacterial membrane to cause activation of compliment (C'). This results in complement-mediated bacteriolysis, or increased opsonization which leads to increased phagocytosis by the mononuclear phagocytic system.

In addition, the efficacy of this vaccine is based on the use of purified siderophore receptor proteins rather than using whole cells. The immune response in animals vaccinated with a purified SRP preparation is about 20 times greater than the immune response to a preparation of whole cell grown under iron-restricted conditions. During gram-negative sepsis, an animal host mounts an immune response to an invading bacteria. Since the major constituent of the cell wall of gram-negative bacteria is made of lipopolysaccharide (LPS), the immune response of an animal is directed to this structure inducing an immunodominant role for the LPS cell wall. Outer membrane proteins such as IROMPs or SRPs that are not dominant proteins on the surface of the bacterial cell wall induce limited immune response resulting in low antibody titers. Thus, the use of a bacterin made of whole bacterial cells grown under iron restriction to express siderophore receptor proteins provides a limited immune response to the siderophore receptor proteins due to competing antigens on the cell surface. By comparison, immunizing an animal with a vaccine made of purified SRPs, there is less antigenic competition and the animal's immune system focuses its response on the receptor proteins. Serological profiles show a significant increase in antibody titer in the SRP-vaccinated group compared to the whole cell-vaccinated group when boosted with whole cell expressing SRP.

Polyclonal antibodies may be raised to the siderophore receptor protein by hyperimmunizing an animal with an inoculum containing the isolated siderophore receptor protein. The blood serum may be removed and contacted with immobilized siderophore receptor proteins reactive with the protein-specific antibodies. The semi-purified serum may be further treated by chromatographic methods to purify IgG and IgM immunoglobulins to provide a purified polyclonal antibody sera for commercial use.

Monoclonal antibodies reactive with the siderophore receptor protein may be raised by hybridoma techniques known and used in the art. In brief, a mouse, rat, rabbit or other appropriate species may be immunized with a siderophore receptor protein. The spleen of the animal is then removed and processed as a whole cell preparation. Following the method of Kohler and Milstein (Nature 256:496–97 (1975)), the immune cells from the spleen cell preparation can be fused with myeloma cells to produce hybridomas. The hybridomas may then be cultured and the culture fluid tested for antibodies specific for siderophore receptor proteins using, for example, an ELISA in which specific siderophore receptor proteins are attached to a solid surface and act as capture antigens. The hybridoma may then be introduced into the peritoneum of the host species to produce a peritoneal growth of the hybridoma, and ascites fluids containing the monoclonal antibody to the bacteria may be collected.

The monoclonal antibodies may be used in diagnostic and therapeutic compositions and methods, including passive immunization. For example, immunoglobulins specific towards a siderophore receptor protein may be used to provide passive immunity against gram negative sepsis. Animals may be treated by administering immunoglobulins intramuscularly at about 100/mg/kg body weight, about every 3–7 days.

A method for diagnosing an infection by gram-negative bacteria in a body sample may be carried out with the polyclonal antibody sera or monoclonal antibodies described hereinabove, in an enzyme-linked immunosorbant assay (ELISA), radioimmunoassay (RIA), immunofluorescent assay (IFA), a Northern, Western or Southern blot assay, and the like. In brief, the antibody or body sample (i.e., tissue sample, body fluid) may be immobilized, for example, by contact with a polymeric material such as polystyrene, a nitrocellulose paper, or other like means for immobilizing the antibody or sample. The other antibody or body sample is then added, incubated, and the non-immobilized material is removed by washing or other means. A labeled species-specific antibody reactive with the later is added. The serum antibody or gram-negative bacteria in the body sample, is then added and the presence and quantity of label is determined to indicate the presence and amount of gram-negative bacteria in the body sample.

The invention will be further described by reference to the following detailed examples, wherein the methodologies are as described below. These examples are not meant to limit the scope of the invention that has been set forth in the foregoing description. Variation within the concepts of the invention are apparent to those skilled in the art. The disclosures of the cited references throughout the application are incorporated by reference herein.

EXAMPLE 1

Production and Purification of Siderophore Receptor Proteins

Escherichia coli serotype 078 (turkey isolate; serotyped by Pennsylvania State University, deposited with the American Type Culture Collection (ATCC), Bethesda, Md., U.S.A., as ATCC #55652, on Jan. 3, 1995) (700 ml at $10^8$ colonies/ml) was inoculated into a Virtis bench-top fermenter (Virtis, Inc., Gardiner, N.Y.), charged with 20-L of brain-heart infusion (BHI, Difco Laboratories, Detroit, Mich.) containing 50 μgrams/ml of dipyridyl (Sigma Chemical Co., St. Louis, Mo.) at 41° C. This isolate has been shown to produce four siderophore receptor proteins for (MW 89 kDa, 84 kDa, 78 kDa, 72 kDa) under iron-restrictive conditions. The pH was held constant at 7.4 by automatic titration with 5N NaOH. The fermenter was stirred at 400 rpm. The culture was grown continuously for 18 hours after which the bacteria were removed by continuous-flow centrifugation at 20,000×g at 4° C. using a Beckman (Model J2-21M) centrifuge (Beckman Instruments, Eden Prairie, Minn.). The pelletized bacteria were washed two times with 1,000 ml physiological saline (0.85%) to remove contaminating culture media proteins.

The bacteria were resuspended in tris-buffered saline (TBS) containing 2.0% sodium N-lauroyl sarcosinate (SARKOSYL™, Sigma Chemical Co., St. Louis, Mo.), optical density 5%, 540 nm. The suspension was incubated at 4° C. for 45 minutes with continuous stirring. The cells were then disrupted using a continuous-flow cell sonicator (Banson 450, Danbury, Conn.) at 4° C., with a maximum flow rate of 5 gph. The disrupted cell suspension was centrifuged at 16,000×g for 20 minutes.

The effluent from the continuous-flow cell sonicator containing the outer membrane proteins was collected and concentrated using ethanol precipitation at −20° C. It is understood that the supernatant may also be concentrated by membrane concentration using a 50,000 MW cut off diaflow membrane (Amicon, Danvers, Mass.). The concentrated material (10% T at 540 nm) was solubilized using 0.2 percent sodium dodecyl sulfate (SDS) in TBS at pH 7.4.

The elution profile of the concentrated material treated with 0.2% SDS is shown in FIG. 1. The solubilized material was applied to a Vantage column (Amicon, Danvers, Mass.) containing 3.2-L of cellufine fast flow GC-700 gel matrix (Amicon, Danvers, Mass.) equilibrated with TBS containing 0.2% SDS at 250° C. Purification of the protein was monitored by UV absorption at 280 nm. Flow rate through the column was 3,000 ml/hr and 15-ml fractions were collected using a UA-5 Detector and Retriever 5 fraction collector (ISCO, Inc., Lincoln, Nebr.). Fractions from each peak were pooled and concentrated using a Diaflo ultrafiltration apparatus with a 50,000 MWCO membrane. Concentrated material from each peak was examined by gel electrophoresis. As shown in FIG. 1, peak 1 contained approximately 85% pure siderophore proteins. This solution was ethanol precipitated at −20° C. for 24 hours to remove the SDS, and then resuspended in phosphate buffered saline (PBS). The amount of protein was determined using a Pierce BCA protein assay (Pierce, Rockford, Ill.).

EXAMPLE 2

Preparation of Vaccine with Siderophore Receptor Proteins

The precipitate from Example 1, hereinabove, containing siderophore receptor proteins of E. coli serotype 078, were resuspended in physiological saline (0.85%) containing 0.1% formalin as a preservative. The protein concentration was 300 µg/ml. The aqueous protein suspension (1,000 ml) was emulsified in a water-in-mineral oil adjuvant containing 972 ml Drakeol 6 mineral oil and 28 ml of Anlacel A as an emulsifier. The mixture was emulsified using an Ultra-Turnax T50 emulsifier (KIKA Works, Inc., Cincinnati, Ohio) at 4° C. The water-in-oil emulsion was stored at 4° C.

EXAMPLE 3

Vaccination of Poultry with Siderophore Receptor Protein Vaccine

Seventy-two turkey poults were raised in isolation from one day of age. At three weeks of age, the birds were divided into two equal groups. Group 1 was vaccinated subcutaneously with the vaccine from Example 2 above, at a dosage level of 150 µg of siderophore receptor protein per bird. Group 2 remained as non-vaccinated controls. Group 1 was given a booster vaccination with the vaccine at a dosage level of 250 µg siderophore receptor protein per bird at 18 days after the first vaccination.

The vaccinated and non-vaccinated birds were equally divided among four isolation rooms. Rooms A and B contained the vaccinated birds, and Rooms C and D contained the non-vaccinated controls. At seven weeks of age, birds in Groups A and C were challenged subcutaneously with *Salmonella agona* at $1.0 \times 10^8$ cfu/bird. At 24, 48, 72, 96 and 120 hours post-challenge, two controls and two vaccinated birds were killed. The spleens were aseptically removed from each bird and individually weighed, and adjusted to 4 grams/spleen, 10 grams/liver. Each sample was then homogenized in sterile physiological saline using a Stomacher Lab Blender, Model 3500 (Seward Medical, London). Serial ten-fold dilutions of each homogenate was plated in duplicate on brilliant sulfur green plates (Difco Laboratories, Detroit, Mich.).

The results show the quantitative clearance of *Salmonella agona* in spleens of SRP-vaccinated and non-vaccinated turkeys (FIG. 2). Time 0 represents the number of bacteria given to each bird. At 24-hours, post-challenge in the vaccinated birds, the level of bacteria were reduced to zero and remained at that level throughout the sampling period. In contrast, the non-vaccinated controls remained positive for the duration of the experiment.

EXAMPLE 4

Cross-Reactivity of Siderophore IROMPS Produced by *Escherichia coli* (Serotype 078)

Hyperimmunized serum produced against purified siderophore receptor proteins was examined for its cross-reactivity to bacteria from different genera and species. Siderophore receptor proteins were produced in the following bacteria: *Escherichia coli* (serotypes 01a, 02a and serotype 078 (ATCC #55652)), *Salmonella agona, Salmonella blockley, Salmonella enteriditis, Salmonella hadar, Salmonella Heidelberg, Salmonella montevideo, Salmonella senftenberg, Salmonella cholerasuis*, and *Pasteurella multocida* (serotype A:3,4; deposited with ATCC as ATCC #55657, on Feb. 14, 1995. These bacteria, except for *S. cholerasuis*, were field isolates obtained from clinically diagnosed birds and serotyped by the State Poultry Testing Laboratory, Willmar, Minn. (*Salmonella spp.*) and Pennsylvania State University (*E. coli*). *Salmonella cholerasuis* was obtained from the University of Minnesota Diagnostic Laboratory. The bacterial isolates were grown in 100 ml of BHI broth with dipyridyl (175 mM), and without dipyridyl but containing 200 μm ferric chloride.

The bacteria were collected from the cell cultures by centrifugation at 16,000×g for 10 minutes at 4° C. The cell pellets were washed twice in tris-buffered saline (TBS) at pH 7.4 and resuspended in 30 ml TBS. The cells were ultrasonically disrupted for 2 minutes at 4° C. using a Branson Ultrasonic Sonicator (Danbury, Conn.). The disrupted cell suspension was centrifuged at 16,000×g for 20 minutes at 4° C. The supernatant was collected centrifuged at 30,000×g for 2 hours at 4° C. The pellet was resuspended in 10 ml TBS containing 2% sodium n-lauroyl sarcosine and placed on a gyratory shaker for 45 minutes at 4° C. The detergent insoluble outer membrane protein-enriched fraction was collected by centrifugation at 30,000×g for 2 hours at 4° C. The pellet was resuspended in 1 ml TBS and stored at −90° C. Proteins were separated by SDS-PAGE with a 4% stacking gel on a 12% resolving gel. Laemmli, U. K., *Nature*, 227:680–685 (1970).

The outer membrane proteins from the different *E. coli*, Salmonella and Pasteurella isolates were transferred from the SDS-PAGE gels to nitrocellulose membranes (Bio-Rad Laboratories, Hercules, Calif.). The membranes were probed with negative (control) and positive antisera to the siderophore receptor proteins.

The control antisera was collected from the birds in group 2, as described in Example 3 hereinabove. The positive antisera was collected from birds in group 1 from Example 3 hereinabove, at 5 days after the second vaccination. The sera, 50 ml each, were absorbed with killed whole cell bacteria (*E. coli 078, Salmonella heidelberg, Pasteurella multocida*) grown in iron-replete media (BHI containing 200 μm ferric chloride) for 1 hour at 4° C.

The SDS-PAGE patterns of the outer membrane protein extracts of the different bacterial isolates, showed expression of siderophore receptor proteins when grown under conditions of iron restriction, in contrast to non-iron restricted controls which did not express siderophore receptor proteins. *Pasteurella multocida* produced three siderophore receptor proteins under conditions of iron restriction which had molecular masses of approximately 96 kDa, 84 kDa and 80 kDa. The *E. coli* isolates produced slight variation in their IROMP profiles. Serotype 078 produced four siderophore receptor proteins with approximate molecular mass of 89 kDa, 84 kDa, 78 kDa and 72 kDa. Serotype 02a produced three bands with molecular weights of 89 kDa, 78 kDa and 72 kDa. Serotype 01a produced two bands with molecular weights of 84 kDa and 78 kDa. All of the Salmonella isolates examined produced three siderophore receptor proteins with identical banding patterns with approximate molecular weights of 89 kDa, 81 kDa and 72 kDa.

Western blot analysis revealed that the positive antisera prepared against the purified siderophore receptor proteins of *E. coli* 078 reacted intensely with the siderophore receptor proteins of *E. coli* serotypes 01a, 02a and the receptor proteins of Salmonella. The 96 kDa and 84 kDa receptor protein of Pasteurella reacted with the positive *E. coli* protein antisera. These results show that the siderophore receptor proteins of *E. coli* have complete antigenic homology to Salmonella and partial homology to *Pasteurella multocida*. The control sera did not react with any siderophore receptor proteins of those species.

EXAMPLE 5

Cross-Reactivity of Siderophore Receptor Proteins of *Escherichia coli* (Serotype 078)

*Escherichia coli* isolates (150 isolates) originating from colisepticemic birds were screened for reactivity with the positive antisera of Example 4, hereinabove. The isolates were examined by direct agglutination using the siderophore receptor antisera and negative reference sera. Ninety-eight percent (98%) of the *E. coli* isolates were agglutinated using the positive antisera in contrast to the negative sera. The positive antisera also reacted with *Pseudomonas aeruginosa, Klebsiella pneumoniae* and five sero groups of Salmonella (serotype B, $C_1$, $C_2$, $D_1$ and $E_3$).

EXAMPLE 6

Serological Response to Siderophore Receptor Proteins (SRP) of *E. coli* in Vaccinated and Non-Vaccinated Flocks Under Natural Field Conditions Fifty one thousand, one-day old turkey poults were equally divided among two barns designated as barns 1 and 2. At six weeks of age, birds in barn 1 were subcutaneously injected with a water-in-oil vaccine as described hereinabove in Example 2. Each bird received 0.5 cc containing 300 µg *E. coli* serotype 078 siderophore receptor protein (SRP) in the lower neck region. Barn 2 remained as non-vaccinated controls. Blood was drawn from 15 birds per barn at weekly intervals.

Figure 3:
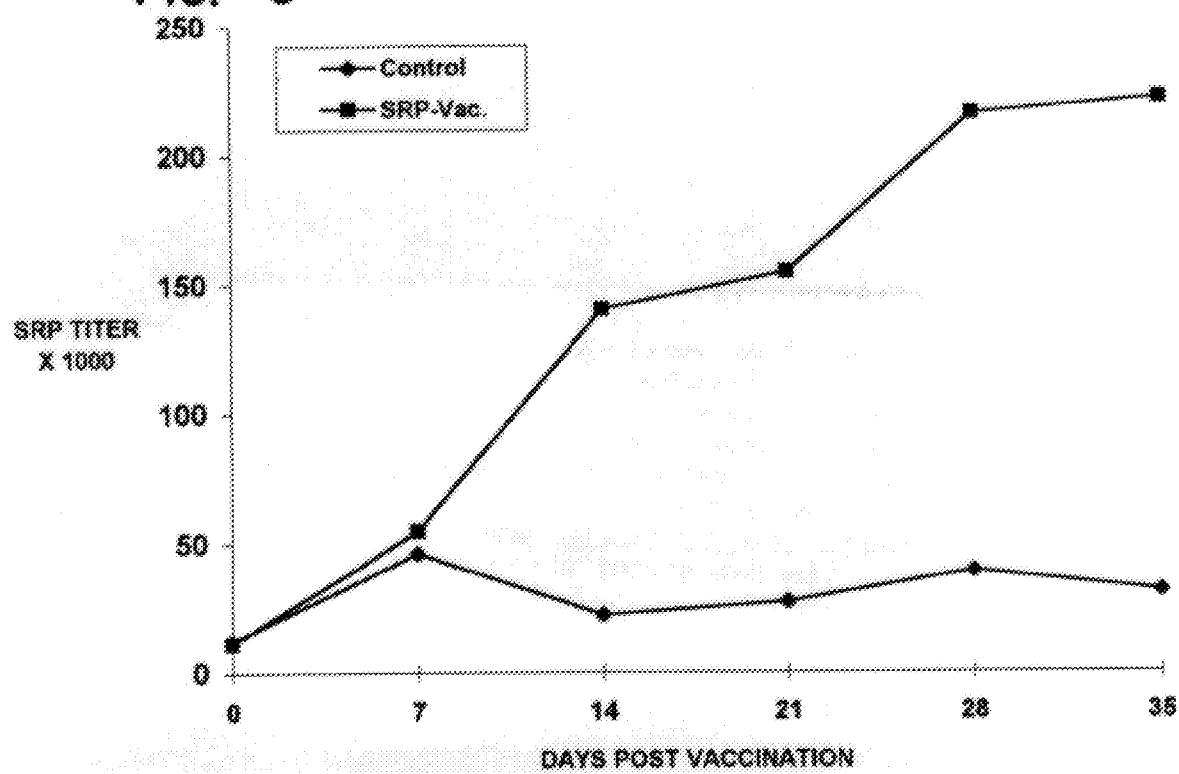
FIG. 3 is a graphic depiction of the serological response to *E. coli* siderophore receptor proteins (SRPS) between vaccinated and non-vaccinated flocks.

FIG. 3 represents the serological response to *E. coli* SRPs between vaccinated and non-vaccinated flocks. The antibody response to the SRPs in the vaccinated flock increased steadily with each sampling period as compared to non-vaccinated controls. At 35 days following vaccination, the vaccinated group had a 7.1 times greater antibody response than the control group.

Table 1, below, shows the average weight of processed birds between the vaccinated and non-vaccinated flocks. There was a statistically greater weight advantage between the vaccinated flock (12.2 lbs/bird) as compared to the non-vaccinated flock (11.8 lbs/bird).

TABLE I

THE AVERAGE BODY WEIGHT BETWEEN SRP-VACCINATED AND NON-VACCINATED TURKEYS AT TIME OF PROCESSING

| Barn 2 (non-vaccinated) | | Barn 1 (SRP-vaccinated) | |
| --- | --- | --- | --- |
| #of Birds/lot | Ave. Body weight (Lbs) | #of Birds/lot | Ave. Body weight (Lbs) |
| 2772 | 11.85 | 1986 | 12.00 |
| 3108 | 11.91 | 3168 | 12.11 |
| 3024 | 11.92 | 3072 | 12.04 |
| 3168 | 11.97 | 3060 | 12.25 |
| 3256 | 11.98 | 3072 | 12.36 |
| 3186 | 11.75 | 3072 | 12.57 |
| 3136 | 11.65 | 3024 | 12.31 |
| 2112 | 11.42 | 3024 | 12.16 |
| Total 23762 | Mean 11.8 | Total 23460 | Mean 12.2 |
| | SD 0.192 | | SD 0.18 |
| | CV 1.63 | | CV 1.54 |

Figure 4:
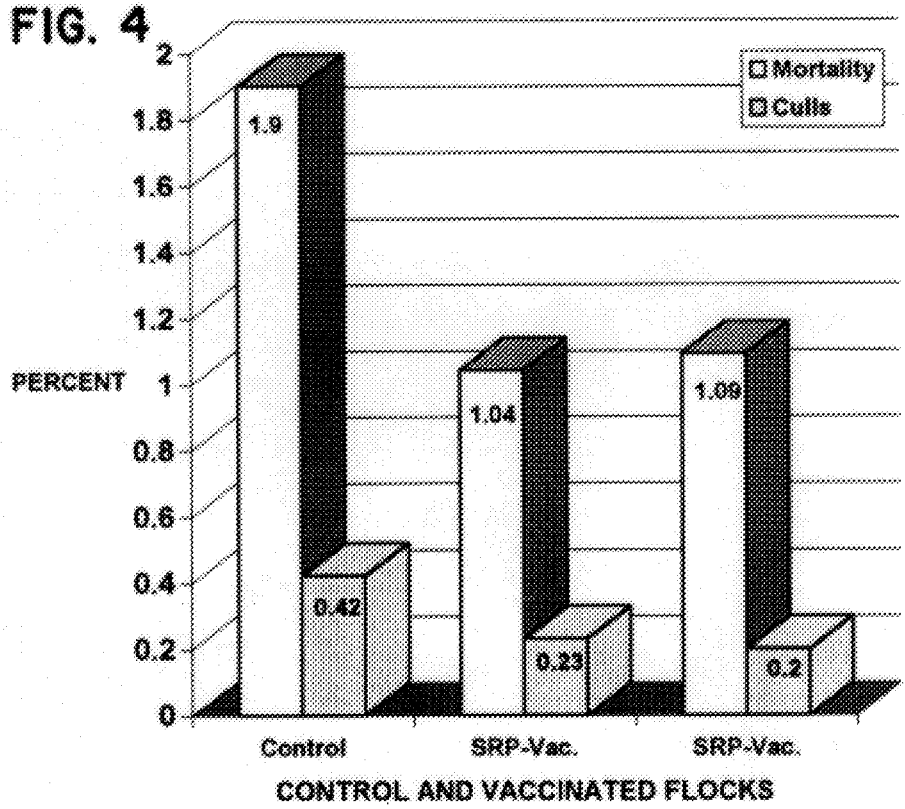
FIG. 4 is a depiction of the total % mortality and culls in control and *E. coli* SRP-vaccinated flocks (3–13 weeks of age).
Figure 5:
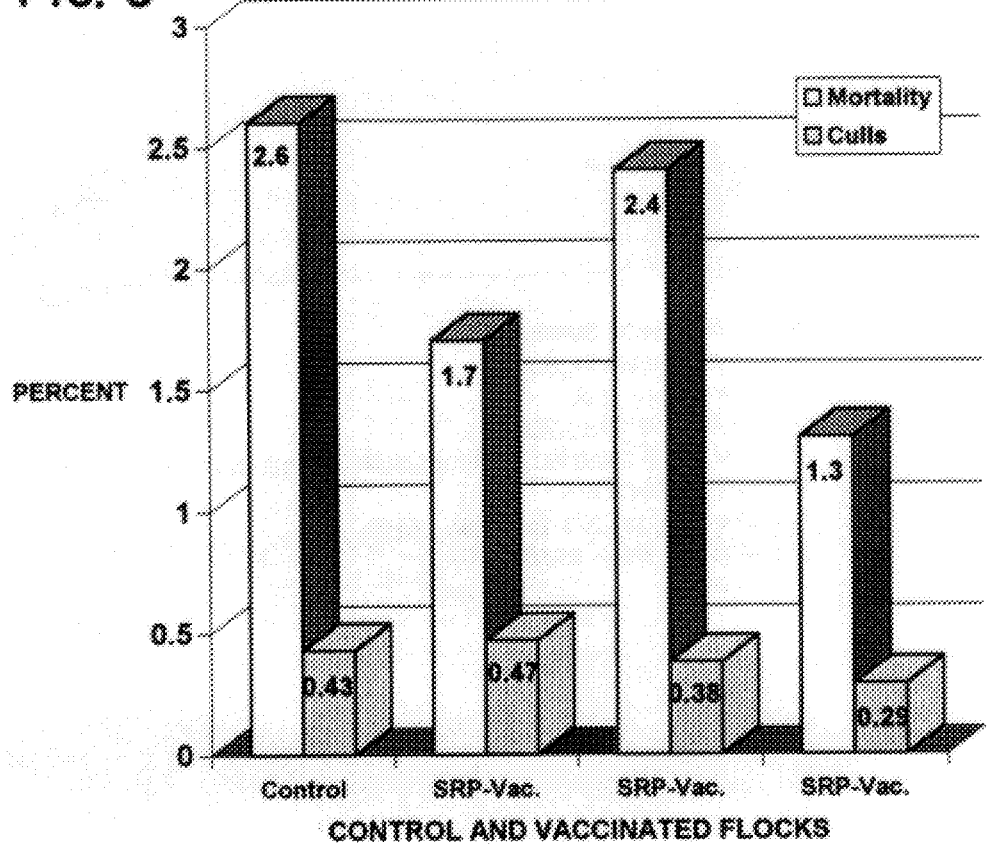
FIG. 5 is a depiction of the total % mortality and culls in control and *E. coli* SRP-vaccinated flocks (3–13 weeks of age).

FIGS. 4 and 5 show the total percent mortality and culls in *E. coli* SRP-vaccinated sister flocks (i.e., originating from the same breeder hens or hatchmates), and the non-SRP-vaccinated controls, from 3–13 weeks of age. These results show the true field mortality after vaccination, by excluding early poult mortality which could result in erroneous results. As can be seen, there was a significant reduction in both mortality and birds culled in the SRP-vaccinated flocks. These results demonstrate the usefulness of *E. coli*-derived siderophore receptor proteins in a vaccine for controlling systemic infections caused by *E. coli* under natural field conditions.

EXAMPLE 7

Cross-Reactivity of SRPs of *Salmonella senftenberg* and *Pasteurella multocida*

Forty-eight Nicholas turkey poults were raised in isolation from one day of age. At three weeks of age, the birds were divided into two equal groups designated as Group 1 and Group 2. Twelve birds in Group 1 were vaccinated subcutaneously with (0.5 cc) 300 µg purified SRP isolated from *Salmonella senftenberg*. The vaccine was prepared as described in Example 2 above. The remaining twelve birds were used as non-vaccinated controls. Birds in Group 2 were treated the same as in Group 1, except 12 of the birds were vaccinated with 300 µg purified SRP isolated from *Pasteurella multocida*.

Blood was taken from all of the birds in both groups at 5 day intervals. Fifteen days after the first injection, vaccinated birds received a second injection of the appropriate SRP. Each vaccinated bird received 500 µg, (0.5 cc) SRP subcutaneously in a water-in-mineral adjuvant. All non-vaccinated birds remained as controls. Birds were bled at 5-day intervals.

Figure 7:
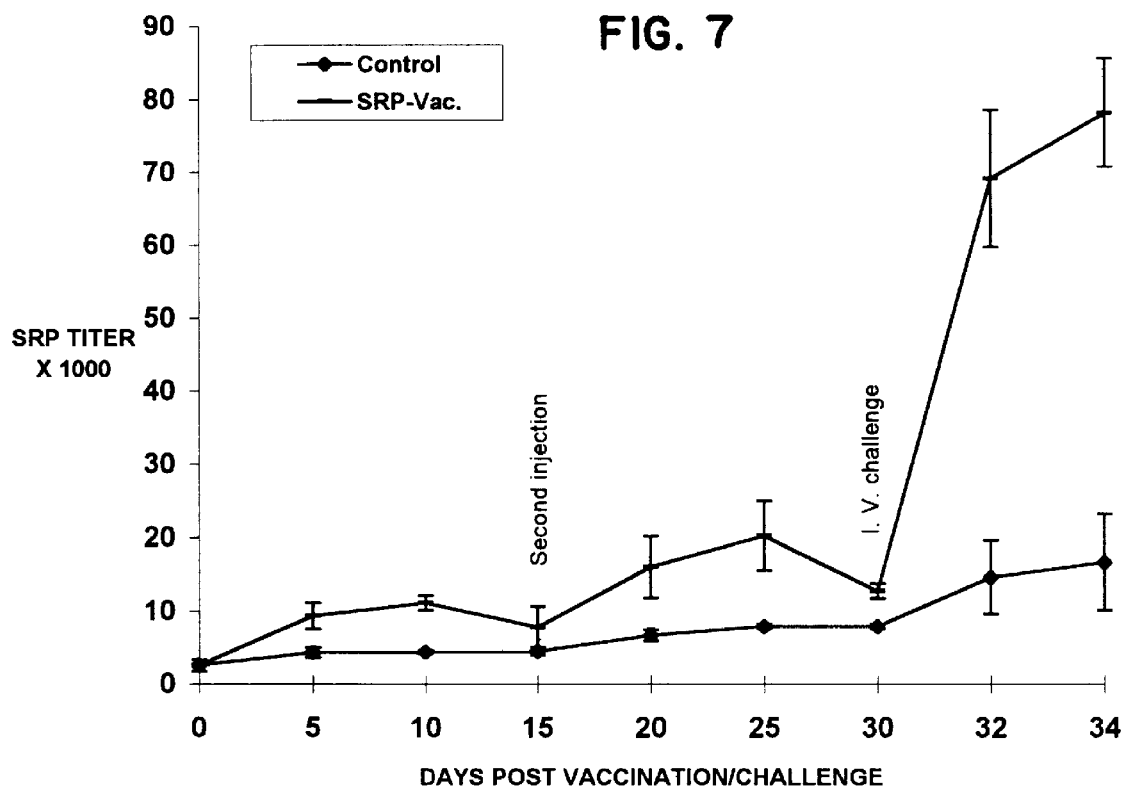
FIG. 7 is a graphic depiction of the serological response in birds vaccinated with purified siderophore receptor proteins from *Salmonella senftenberg*, showing cross-reactivity with the SRP of *E. coli*.

Fifteen days after the second injection, the vaccinated birds in Group 1 were intravenously challenged with 100 µg *S. heidelberg* SRP (FIG. 7). Blood was taken at 2-day intervals post challenge. There was a high antibody response to challenge at 2- and 4-days post challenge. This data shows the cross-reactivity of *S. heidelberg* to *S. senftenberg*. These proteins, in turn, both cross-react with *E. coli*, as demonstrated by the ELISA using *E. coli* SRPs as the capture antigen according to the protocol described hereinabove in Example 5.

Figure 6:
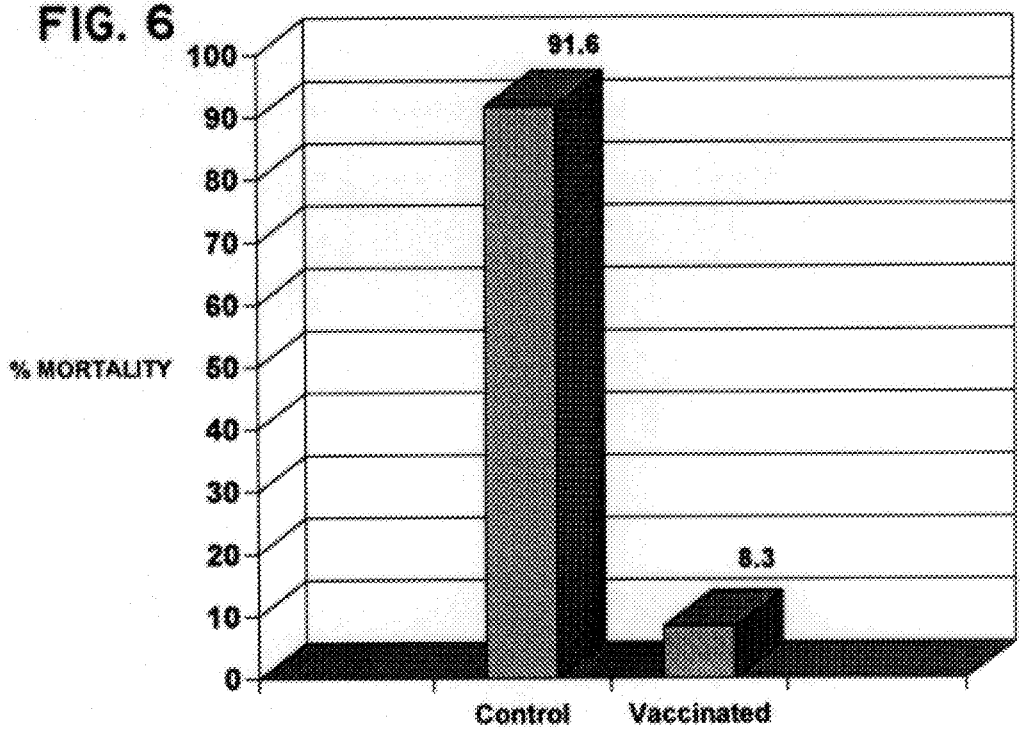
FIG. 6 is a graphic depiction of the total mortality in SRP-vaccinated and non-vaccinated turkeys following challenge with *Pasteurella multocida* P-1059.

Likewise, 15 days after the second injection, all birds in Group 2 were challenged intramuscularly with $1.1 \times 10^6$ CFU of *P. multocida*, ATCC strain P-1059. Mortality was recorded daily for 2 weeks post-challenge. FIG. 6 and Table 2 below also shows the mortality between the vaccinated and non-vaccinated birds following challenge.

TABLE 2

Mortality of Vaccinated and Non-Vaccinated Turkeys Following Challenge with *Pasteurella multocida* P-1059

| Numbers of dead/total tested | |
| --- | --- |
| Non-vaccinated | Vaccinated |
| 11/12 (91.6%) | 1/12 (8.3%) |

Eleven (91.6%) of the non-vaccinated birds died within 14 days after challenge (see, FIG. 6). In contrast, only 1 (8.3%) of the birds in the vaccinated group died. These results demonstrate that siderophore receptor proteins can be used as protective immunogens.

Figure 8:
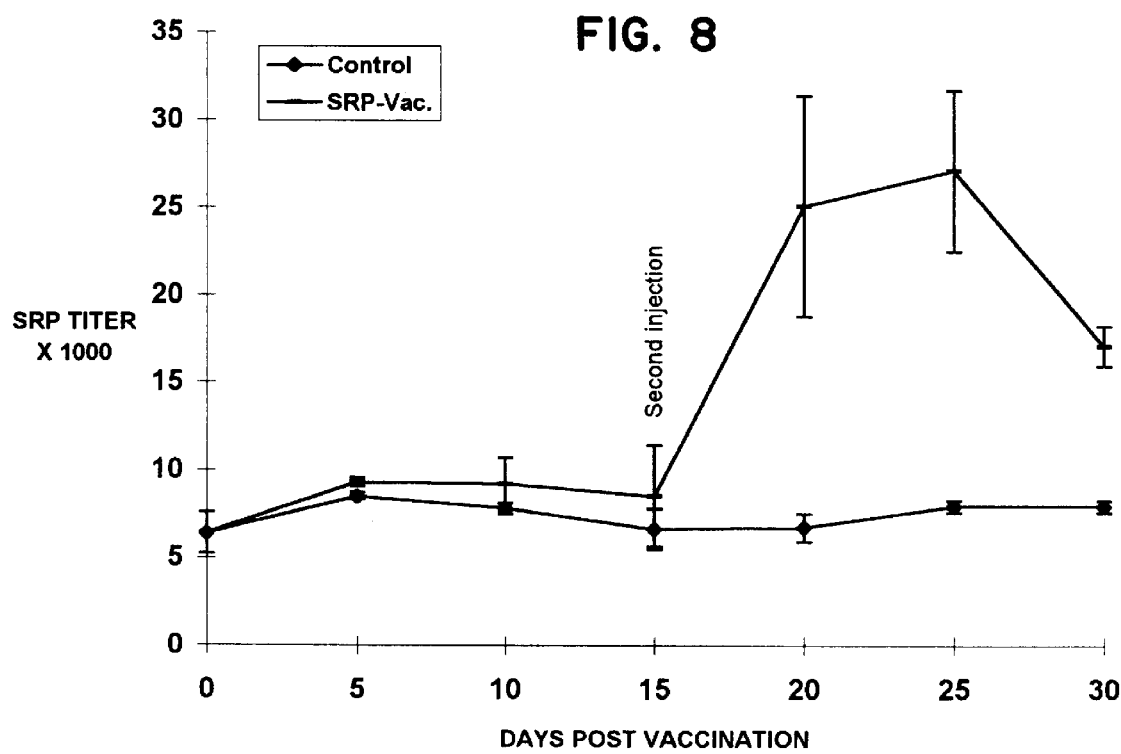
FIG. 8 is a graphical depiction of the serological response in birds vaccinated with purified siderophore receptor proteins from *P. Multocida*, showing cross-reactivity with the SRP of *E. coli*.

FIGS. 7 and 8 show the serological response of birds vaccinated with siderophore receptor proteins isolated from *S. senftenberg* and *P. multocida*, respectively. The siderophore receptor proteins induced primary and secondary immune responses in both vaccinated groups at 10 and 20 days post-vaccination as compared to non-vaccinated control birds. These antibody responses demonstrate the cross-reactive nature of these protein, which was confirmed in the ELISA assay using SRPs isolated from *E. coli* as capture antigens.

EXAMPLE 8

Cross-Reactivity of Siderophore Receptor Proteins as Evaluated by ELISA

The cross-reactivity of *E. coli* siderophore receptor proteins from Example 7 above was further examined using an Enzyme-Linked Immunosorbent Assay (ELISA). The siderophore receptor proteins (SRPs) were purified from polyacrylamide gels using a model 422 electro-eluter (Bio-Rad Laboratories, Hercules, Calif.). The proteins were then used as capture molecules in an indirect ELISA test.

The optimum working concentrations of SRP and conjugate was determined by several chequerboard titrations using positive and negative control serums from Example 6 above. A prediction curve was then established to calculate SRP ELISA titers at a 1:200 dilution. All subsequent tests were performed at a single serum dilution (1:200) and SRP titers were calculated from the average of duplicate test absorbance values.

The ELISA was performed by adding 100 µl of diluted SRP of E. coli in 0.05M (0.1 ug) carbonate buffer (pH 9.6) to each well of a 96-well flat-bottom, easy wash microtiter plate (Corning, Corning, N.Y.). After overnight incubation at 4° C., excess SRP was removed and the plate was washed. All subsequent washing steps were done three times in phosphate-buffered saline (pH 7.4) with 0.05% Tween 20. The plates were blocked for one hour at 37° C. with 4% Fish Gelatin (Sigma) in PBS and then washed.

Duplicate serum samples from Example 7 were tested in parallel at single-point dilutions using 100 µl/well and incubated for 40 minutes at 37° C. Each plate contained positive and negative control sera obtained from birds from Example 4 above. After washing, 100 µl peroxidase-labeled conjugate was added to each well. After incubation for 40 minutes at 37° C., the plates were washed and 100 µl of ABTS peroxidase substrate in buffered $H_2O_2$ solution (Kirkegaard & Perry Laboratories Inc., Gaithersburg, Md.) was added to each well. The substrate was allowed to react for 15 minutes at room temperature. The reaction was terminated with 50 µl of 1% SDS and the absorbance read directly using a MR650 microtiter plate reader (Dynatech Laboratories, Alexandria, Va.).

EXAMPLE 9

Fermentation protocol for production of siderophore receptor proteins

The following protocol was used to culture E. coli 078 (ATCC #55652) resulting in expression of six (6) siderophore receptor proteins.

An E. coli master seed stock was prepared by growing the organism in 2000 ml of sterile BHI broth containing 1–500 µg 2,2'-dipyridyl for 8 hours at 37° C. The bacteria were harvested by centrifugation at 10,000×g for 30 minutes. The culture is washed twice by centrifugation and resuspending the pellet in sterile PBS. The final pellet was resuspended into 500 ml sterile BHI containing 20% sterile glycerol. One milliliter of culture was transferred to a 2-ml cryovial and stored at −85° C.

A cryovial (1 ml) of the E. coli master seed stock was used to inoculate a 100-ml culture flask containing tryptone (10 g/l), yeast extract (5 g/l), dextrose (2 g/l), NaCl (10 g/l), and 2,2'-dipyridyl (15.0 µg/ml). The culture was incubated at 37° C. for 7 hours, at which time it was inoculated into 2 liters of the above media and allowed to grow for an additional 4 hours at 37° C. The 2-liter culture was used to inoculate a 20-liter Virtis bench-top fermenter (Model 233353, Virtis, Gardiner, N.Y.) charged with 13 liters of the above-described media. The pH was held constant between 6.9 and 7.2 by automatic titration with 30% NaOH and 10% HCl. The stirring speed was 250 rev/minute, and the culture was aerated with 11 liters/minute at 34° C. Foaming was controlled automatically by the addition of 0.4% silicone defoamer (Antifoam-B, J. T Baker, N.J.). The culture was allowed to grow continuously at these conditions for 12 hours (O.D. 600 nm=7.10) at which time it was pumped into a 150-liter fermenter (W. B. Moore, Easton Pa.) charged with 110 liters of the above-described media containing 26.7 µg/ml dipyridyl and 0.2% defoamer. The conditions in the fermenter were as follows: 450 rpm, 50 slpm air, 10 psi backpressure, 34° C., and pH held at 6.9 with NaOH.

After 12 hours of fermentation, the bacteria were inactivated by the addition of 0.15% formalin. The bacteria were harvested by continuous flow centrifugation (20,000×g at 4° C.) using two Beckman (Model J2-21M) centrifuges equipped with JCF-Z continuous flow rotors.

The pelletized bacteria were then washed to remove contaminating culture media proteins and further processed as described above in Example 1. The concentrated material was treated with 0.2% SDS and eluted as described above in Example 1. The peak from the elution profile containing approximately 85% pure siderophore receptor proteins was ethanol precipitated to remove SDS, and resuspended in PBS.

The material was separated by SDS-PAGE as described above in Example 4 with a 4% stacking gel on 12.5% acrylamide gel. The SDS-PAGE pattern of the outer membrane protein extract showed expression of SRPs having molecular weights of 91–92 kDa, 89 kDa, 84 kDa, 78 kDa, 74 kDa and 72 kDa.

EXAMPLE 10

Efficacy of vaccine of SRPs from *Escherichia coli* under natural field conditions The efficacy of vaccinating turkeys with E. coli siderophore receptor proteins (SRPs) under natural field conditions was shown as follows. A farm complex with a history of disease was chosen for experimental trials. The facility was a three state operation, having two brooding barns and eight finishing farms.

Data was collected for one year prior to vaccination to establish an accurate profile on mortalities and bird performance (flocks 1–16 before vaccination). Vaccinating with SRPs was evaluated for a period of 6 months (flocks 17–24 after vaccination). A total of 24 flocks comprising 1,160,864 birds was examined. Vaccination trials began in January and ran through July, considered to be a critical time period for E. coli infections and other natural field challenges.

Brooder barns 1 and 2 were divided in half and designated as A and B (barn-1) and C and D (barn-2). Approximately 50,000 randomized hens were placed in each barn so that each flock contained 25,000 birds. All flocks were vaccinated by subcutaneous injection at 3 weeks of age with a vaccine preparation containing SRPs (MW 91–92 kDa, 89 kDa, 84 kDa, 78 kDa, 74 kDa and 72 kDa, SDS-PAGE on 12.5% acrylamide gel) isolated and purified from E. coli 078 as described above in Example 1. Flocks A and C were vaccinated with a dosage level of 300 µg SRP and $10^9$ $TCID_{50}$ Newcastle Disease Virus (NDV) in a water-in-oil emulsion. Flocks B and D were the controls, and given a dosage level of $10^9$ $TCID_{50}$ NDV only.

At 4 weeks of age, the birds were moved into four second-stage barns while maintaining identity. At nine weeks of age, the birds were moved to four finishing barns, keeping identity on each 25,000 bird flock. Birds were marketed at 12- and 14-weeks of age and identity was maintained throughout processing.

Table 3 shows the cumulative farm history before and after SRP-vaccination. Twenty-four flocks were evaluated, the 16 before vaccination (1–16) and the 8 vaccinated flocks (17–24) including controls. Flocks 1–16 were not SRP-vaccinated and included as a farm history to show the performance advantage to SRP-vaccinated flocks 17–24.

Table 3 below, shows the age at which each flock was marketed, the head count, total percent mortality, condem (i.e., condemnation at processing), and average bird weight/lot processed.

TABLE 3

| Flocks | Age (days) | Head Count | Mortality (%) | Condem (%) | Ave. wt. |
|---|---|---|---|---|---|
| Flock History Before SRP-vaccination | | | | | |
| 1 | 97 | 47818 | 8.37 | 1.13 | 13.88 |
| 2 | 94 | 45638 | 12.53 | 1.17 | 13.80 |
| 3 | 95 | 51443 | 12.87 | 3.44 | 13.58 |
| 4 | 96 | 49999 | 4.20 | 1.23 | 13.86 |
| 5 | 92 | 49733 | 4.68 | 0.96 | 13.25 |
| 6 | 96 | 48303 | 7.36 | 1.25 | 13.49 |
| 7 | 101 | 48722 | 16.50 | 2.12 | 15.10 |
| 8 | 103 | 51456 | 12.26 | 1.41 | 15.60 |
| 9 | 98 | 50423 | 7.84 | 1.63 | 14.73 |
| 10 | 96 | 50880 | 7.04 | 1.59 | 13.81 |
| 11 | 95 | 46710 | 14.85 | 1.16 | 14.04 |
| 12 | 98 | 48994 | 11.32 | 1.09 | 13.89 |
| 13 | 92 | 43433 | 21.28 | 1.74 | 13.23 |
| 14 | 94 | 49806 | 9.59 | 1.08 | 13.64 |
| 15 | 93 | 39216 | 28.08 | 2.35 | 12.92 |
| 16 | 96 | 46119 | 15.95 | 1.45 | 13.76 |
| Flock History After SRP-vaccination | | | | | |
| 17 | 99 | 48323 | 8.08 | 1.45 | 15.37 |
| 18 | 96 | 48091 | 8.15 | 1.16 | 14.93 |
| 19 | 96 | 48748 | 6.89 | 1.07 | 16.16 |
| 20 | 90 | 48462 | 7.36 | 1.06 | 14.11 |
| 21 | 92 | 49175 | 6.11 | 1.00 | 15.08 |
| 22 | 90 | 48261 | 7.86 | 0.83 | 14.38 |
| 23 | 94 | 51813 | 5.95 | 0.92 | 15.52 |
| 24 | 98 | 49296 | 9.44 | 1.08 | 16.10 |
| Mean | 96/94 | 48043/49021 | 12.2/7.5 | 1.6/1.07 | 13.9/15.3 |
| SD | 2.9/3.5 | | 6.2/1.2 | 0.63/0.18 | 0.70/0.77 |
| CV | 3.1/3.7 | | 51.4/15.5 | 40.9/17.2 | 5.0/5.0 |

Figure 9:
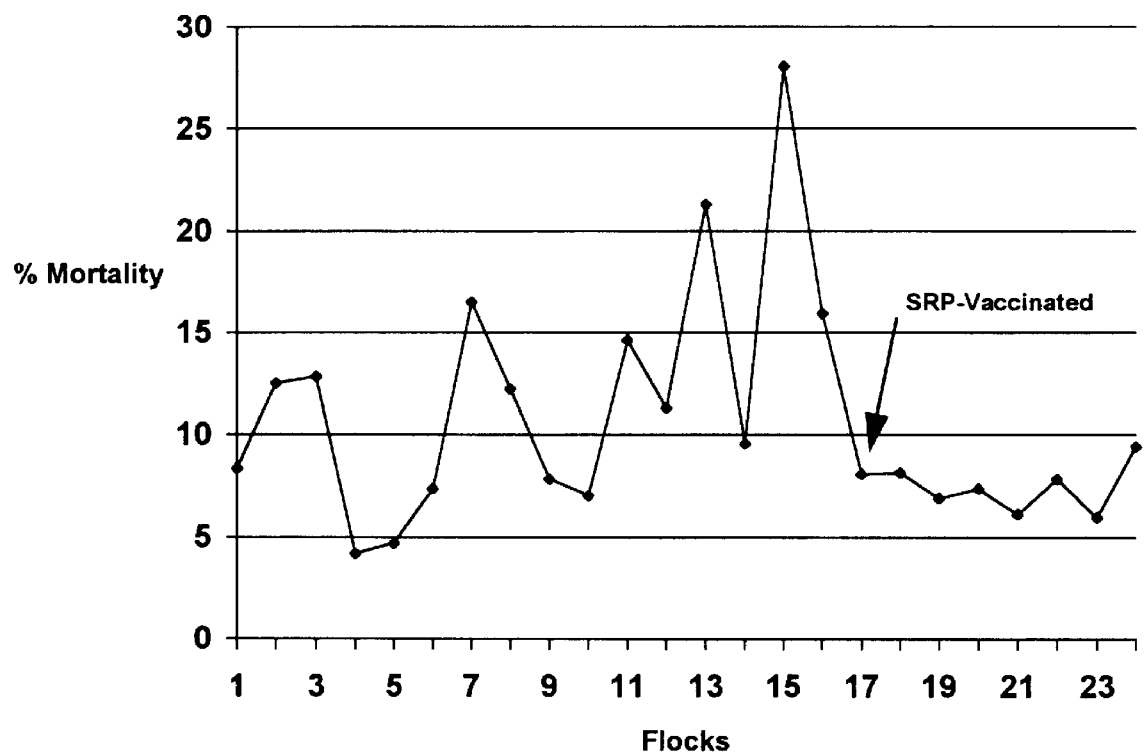
FIG. 9 is a graphic depiction of the total % mortality in consecutive flocks before and after vaccinating with siderophore receptor proteins derived from *E. coli* 078.

As shown above in Table 3, the average percent mortality before vaccination was 12.2±6.2 with a coefficient of variation (cv) of 51.4% as compared to the average mortality after vaccination of 7.5±1.2 with a cv of 15.5%. This is a 4.7% decrease in mortality, which equates to 4700 birds for every 100,000. The decrease in the coefficient of variation (51.4% as compared to 15.5%) on total mortality illustrates a positive effect on bird livability and uniformity. FIG. 9 is a graphical representation of mortalities in consecutive flocks before and after vaccination.

Condemnation was also positively effected showing 1.6±0.63 percent before vaccination as compared to 1.07±0.18 percent after vaccination (Table 3 above). The difference, 0.53% is significant considering the number of birds processed.

A dramatic effect that was observed by the SRP vaccination was the increased weight advantage, as seen above in Table 3. Before vaccination the average bird weight was 13.9±0.70 pounds, with an average growing time of 96 days. The average weight per bird after vaccination was 15.3±0.77 pounds, with an average growing time of 94 days. These results demonstrate the advantage in performance that can be obtained through SRP-vaccination.

Figure 10:
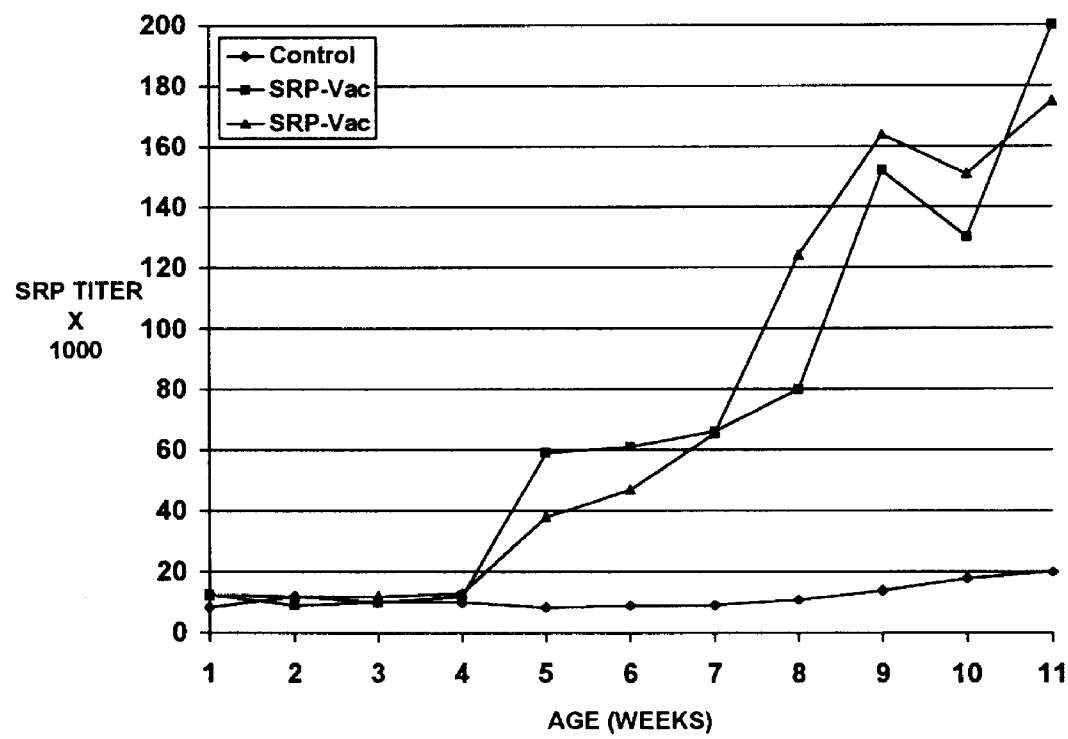
FIG. 10 is a graphic depiction of the serological response to SRPs from *E. coli* between SRP-vaccinated and non-SRP-vaccinated commercial turkey flocks.

FIG. 10 shows the serological response to SRPs of E. coli between the SRP-vaccinated and non-SRP-vaccinated flocks as determined by ELISA, using purified E. coli SRPs as the capture molecule. The assay was conducted as described above in Example 8. The profile was consistent between the vaccinated and non-vaccinated flocks under natural field conditions. As the profile illustrates, once the bird's immune system becomes focused to recognize these proteins, continuous field challenge by bacteria expressing SRPs causes a steady rise in antibody titer to a level which provides protection and/or to the point where systemic challenge does not effect performance.

Using purified IROMPs in a vaccine optimizes the animal's immune system to focus on those proteins. The birds vaccinated with 300 μg purified SRP at three weeks of age showed an increase in titer at 11 weeks of age which was 10,000 times greater than the titer in the non-SRP-vaccinated controls. This increase in titer is the result of focusing the immune system to recognize these proteins. Once vaccinated, the bird establishes a population of memory cells that are activated upon each field challenge. Under natural field conditions, the bird is continuously challenged by gram-negative bacteria such as E. coli, which express SRPs that cross-react and cause a continuous rise in antibody titer (as was seen in the SRP-vaccinated birds). By comparison, the control birds under the same conditions, show low antibody titers even though exposed to the same field challenges.

EXAMPLE 11

Vaccination with SRP-vaccine and vaccine made with bacterial whole cells

A comparison was made between turkeys injected with a vaccine made of purified SRPs derived from *Salmonella heidelberg* prepared as described above in Example 1, and a vaccine made of bacterial whole cells of the same organism grown under iron-restrictions so as to express SRP on the cell surface. The whole cell bacteria was prepared as described in Example 1, except for the following modification: after the fermentation process 0.3% formalin were added to the vessel to kill the organism. The killed bacteria were collected as described in Example 1, washed and resuspended in physiological saline, and adjusted to an optical density of 35% T at 540 mm to give approximately $10^7$ bacteria/ml. The vaccine was prepared as described above in Example 2.

Forty-five thousand one-day old hybrid turkey poults (hens) were raised to 4 weeks of age, on a brooding facility. At four weeks of age, the birds were moved to a growing facility and equally divided among two barns designated as barns 1 and 2. At 6 weeks of age, birds in barn 1 were vaccinated subcutaneously in the lower neck with 0.5 cc of the SRP vaccine while the birds in barn 2 were vaccinated with the whole cell preparation. Blood was taken from 12 birds/barn at weekly intervals to monitor the serological response to SRP between the two groups.

Figure 11:
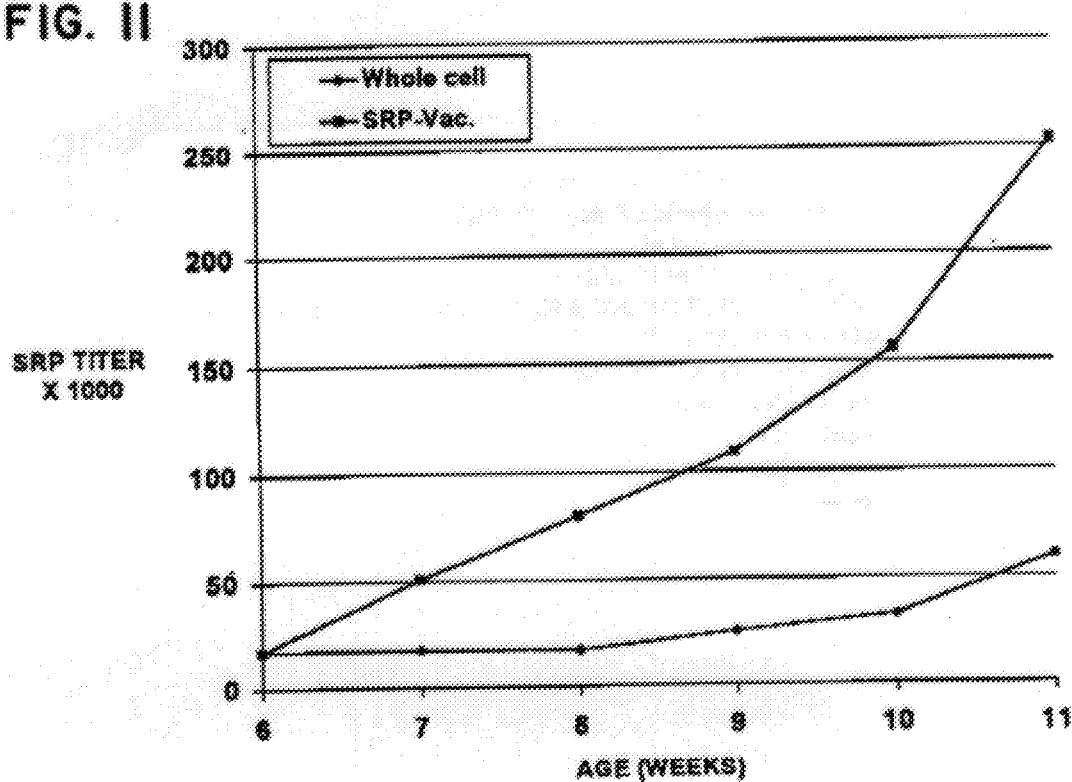
FIG. 11 is a graphical depiction of the serological response of purified SRP and whole cell of *Salmonella heidelberg*.

FIG. 11 shows the titer to SRP between whole cell and SRP-vaccinated birds. The immunological response to SRP was significantly greater in purified SRP-vaccinated group as compared to the whole cell vaccinated group. These results clearly demonstrate the efficacy of using a substantially pure preparation of SRP for inducing an immune response in an animal in contrast to using whole cell expressing the same SRP.

EXAMPLE 12

Transfer of anti-SRP antibodies to Breeder Hen Progeny

The 10-day mortality in progeny from SRP-vaccinated and non-vaccinated breeder hens was evaluated to assess the transfer of anti-SRP antibodies from adult to progeny.

Twenty thousand randomized Nicholas turkey poults (hens) were equally divided among two brooder barns designated as barns 1 and 2. At four weeks of age, all birds in barn 1 were vaccinated with 300 μg of E. coli SRP and Newcastle Disease Virus (NDV) in a water-in-oil vaccine. Birds in barn 2 were given NDV only and acted as controls. At 24 weeks of age, the birds from barn 1 were given a second injection of SRP at 300 μg/bird. Birds from barn 2 remained as non-vaccinated controls. At thirty weeks of age, the birds were placed in barns 1 and 2 of a laying farm. At mid-lay, eggs were collected from the SRP-vaccinated and non-vaccinated hens. Eggs were set in separate incubators and hatchers. At hatch time, all poults were treated the same and identity was maintained throughout sexing and servicing.

Five thousand poults (hens) from each group were placed in a commercial brooding barn and kept in brooding rings at 7 rings/group containing 714 poults/ring. Poult mortality was monitored for each ring/group for a period of 10 days.

Figure 12:
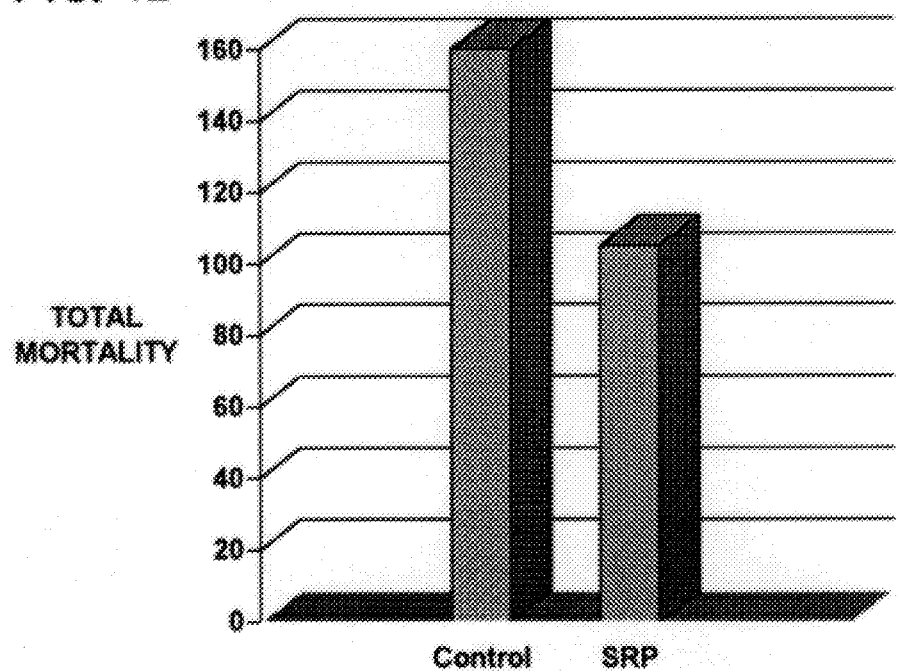
FIG. 12 is a graphic depiction of the total mortality between progeny of SRP-vaccinated and non-vaccinated (control) breeder hens.

The total 10-day mortality in poults originating from the SRP-vaccinated hens was 105 (2.1%) as compared to 160 (3.2%) in the non-vaccinated progeny (FIG. 12). This is a 1.1% advantage in poult livability, which equates to 1100 poults for every 100,000. This is significant considering that there are 200 million turkeys in the United States and 7 billion broilers worldwide.

These results show the beneficial effect of vaccinating breeding stock to induce maternal antibody to SRP in progeny to reduce gram-negative infections that are responsible for much of the early poult mortality.

EXAMPLE 13

Cross-reactive and cross-protective nature of siderophore receptor proteins (SRP) between different serogroups of salmonella The SRP of *Salmonella enteritidis* (Se), serogroup $D_1$ and *Salmonella typhimurium* (St), serogroup B were examined for their ability to cross-react and cross-protect. Briefly, 160 randomized hybrid turkey poults (hens) were raised in isolation. At three weeks of age, the birds were equally divided among 4 isolation rooms, 40 birds/room, designated as A, B, C and D. Birds in group C were subcutaneously injected with a water-in-oil vaccine, as described hereinabove in Example 2, containing 300 μg SRP of *S. typhimurium*. Birds in room D were subcutaneously injected with 300 μg SRP of *S. enteritidis*. Birds in rooms A and B remained as non-vaccinated controls. Blood was taken from 10 birds/group at weekly intervals to monitor the serological response to SRP.

Twenty one days after the first injection, birds in groups C and D were given a second injection containing 300 μg of the appropriate SRP. Blood was taken at 5 and 10 days after the second injection. The serological response to SRP was examined by ELISA using E. coli SRP as the capture molecule as described above in Example 8.

Figure 13:
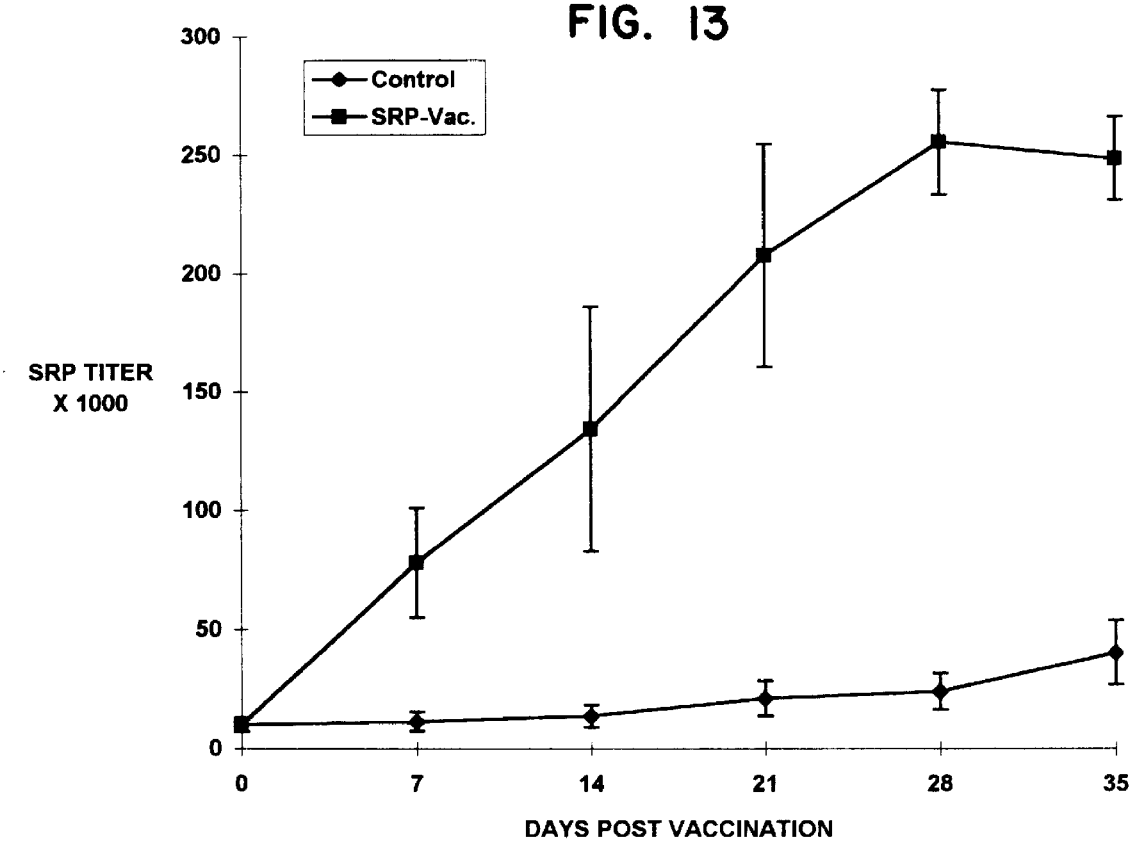
FIG. 13 is a graphical depiction of the serological response in birds vaccinated with purified siderophore receptor proteins from *Salmonella typhimurium*, showing cross-reactivity with the SRP of *E. coli*.
Figure 14:
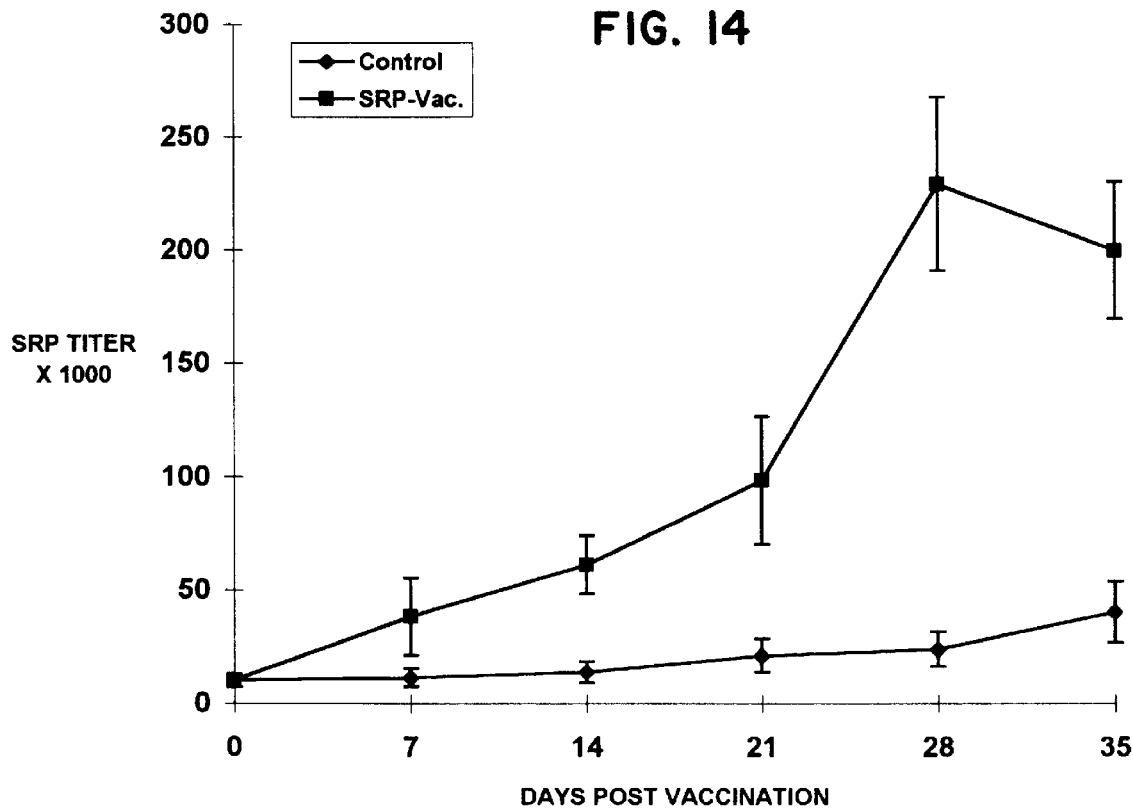
FIG. 14 is a graphical depiction of the serological response in birds vaccinated with purified siderophore receptor proteins from *Salmonella enteritidis*, showing cross-reactivity with the SRP of *E. coli*.

FIGS. 13 and 14 show the serological response of birds vaccinated with SRP isolated from *S. typhimurium* and *S. enteritidis*. The immunological response to SRP increased steadily in both groups with each sampling period as compared to the non-vaccinated controls, showing the immunogenicity of these proteins. Importantly, these results show the cross-reactive nature of these proteins since the ELISA is using E. coli SRP as the capture molecule.

Fifteen days after the second injection, all birds were intravenously challenged with a nalidixic acid resistant strain of *S. enteritidis* or *S. typhimurium* at $5.0 \times 10^7$ colony forming units (CFU)/bird. These bacteria were made resistant to nalidixic acid to enhance their isolation by incorporating nalidixic acid in the recovery media which eliminated any contamination. Bacteria resistant to nalidixic acid were prepared as follows: One ml of a 12-hour Tryptic soy broth (TSB) culture of *S. enteritidis* and/or *S. typhimurium* containing approximately $10^8$ viable organisms, was spread over the surface of a brilliant sulfur green (BSG) agar (Difco) plate containing 500 μg/ml nalidixic acid (Sigma). The plates were incubated at 37° C. for 24 hours and the colonies that grew were cloned by plating on BSG containing 250 μg/ml nalidixic acid. The nalidixic acid-resistant strains of salmonella were incubated in 100 ml of TSB at 37° C. for 12 hours At the end of incubation, the culture was centrifuged (10,000×g) and washed twice in PBS (pH 7.4), and the optical density was adjusted to 35% transmission at 540 nm to obtain $5.0 \times 10^7$ CFU/ml. These isolates were then used for challenge.

To evaluate homologous and heterologous protection, twenty birds in room C (vaccinated with St-SRP) were wing banded and moved into room D, and 20 birds in room D (vaccinated with Se-SRP) were wing banded and moved to room C. All birds in room C (20 St-vaccinated and 20 Se-vaccinated) were challenged with *S. typhimurium*, while birds in room D (20 Se-vaccinated and 20 St-vaccinated) were challenged with *S. enteritidis*.

At 24, 48, 72 and 96 hours post-challenge, two birds from each group were killed. The spleens were aseptically removed from each bird and individually weighed, and adjusted to 4 grams/spleen. A fecal sample from the cecal junction from each bird was also taken. Each sample was weighed and adjusted to 0.5 grams. Four milliliters of sterile saline was added to each spleen and 0.5 ml to each fecal sample. Each sample was homogenized using a Stomacher Lab Blender (Sewert Medical, London) for 1 minute. Serial ten-fold dilutions of each homogenate were plated in duplicate on BSG plates containing 250 μg/ml nalidixic acid.

Figure 15:
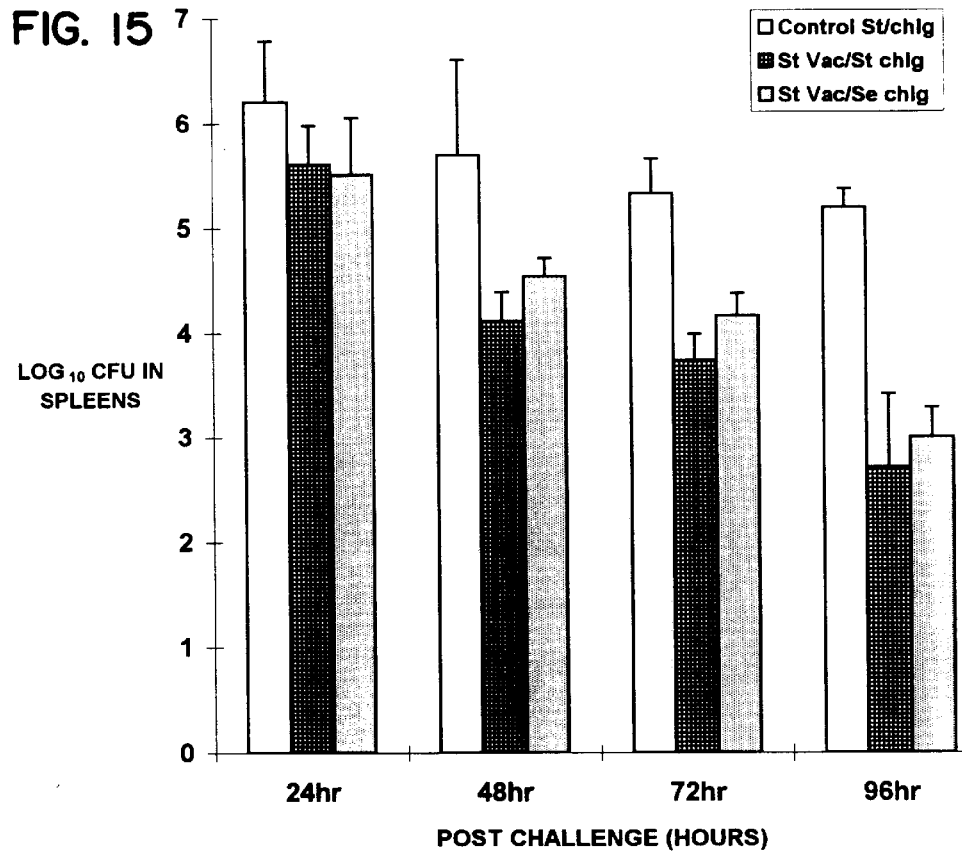
FIG. 15 is a graphical depiction of SRPs of *Salmonella typhimurium* as a protective immunogen against a homologous and heterologous challenge in turkeys.
Figure 16:
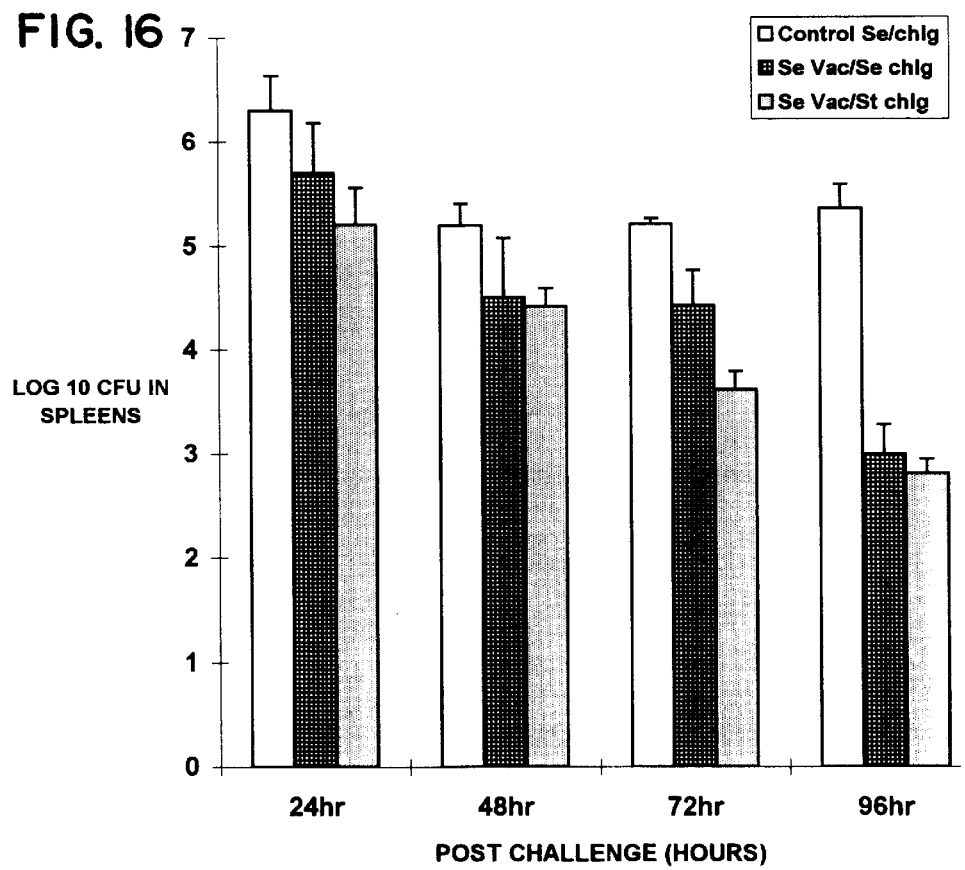
FIG. 16 is a graphical depiction of SRPs of *Salmonella enteritidis* as protective immunogens against a homologous and heterologous challenge in turkeys.

The results show the quantitative clearance of *S. typhimurium* (St) (FIG. 15) and *S. enteritidis* (Se) (FIG. 16) in spleens of SRP-vaccinated and non-vaccinated turkeys. As shown in FIGS. 15 and 16, there was a steady decline in the number of bacteria/spleen. At 96 hours after challenge (chlg), the difference between the vaccinated and non-vaccinated groups was approximately 2.5 logs. An important aspect of these results is the cross-protective nature induced by these proteins. FIG. 15 shows the cross-protective nature of the birds vaccinated with the SRP of Se but challenged with St. FIG. 16 shows this same cross-protective effect of birds vaccinated with SRP of Se and then challenged with St. All vaccinated groups showed a significant reduction in the number of bacteria in spleens in contrast to the non-vaccinated birds.

At 72 and 96 hours after challenge, intestinal shedding of Salmonella was detected in the non-vaccinated birds at greater then log 4. In contrast, all of the vaccinated birds were negative for Salmonella within this same sampling period. These results indicate that these proteins may have some beneficial effect in preventing the intestinal colonization of Salmonella.

EXAMPLE 14

Preparation and use of the 37–38 kDa transmembrane and porin proteins in a vaccine The transmembranes and porin proteins (MW 34–38 kDa), identified as OmpA, OmpC, OmpD and OmpF are expressed with and without iron. These proteins can be purified as described above in Example 1, by collecting fractions 1650–2250 as shown in FIG. 1. These proteins can be combined with peak 1 (FIG. 1) to obtain a combination of SRP and porin proteins that are conserved among Salmonella, E. coli, and Pasteurella.

A vaccine containing E. coli SRPs (MW 89 kDa, 84 kDa, 78 kDa and 72 kDa) was combined with porins (MW 34 kDa–38 kDa) to give a total protein content of 600 μg/ml, and prepared as described above in Example 2. The vaccine was used to induce hyperimmunized sera. Briefly, six (6) three-week old turkeys were given a single subcutaneous injection in the lower neck region followed by a second injection 15 days after. Serum was collected 10 days after the second injection.

Western blot analysis, as described above in Example 4, using sarcosine cell wall extracts of E. coli, Salmonella and Pasteurella and probed with the above sera revealed cross-negative proteins in the 34 kDa and 38 kDa region as well as the SRPs from each isolate examined.

These results indicate the potential of using conserved protein (SRP and porins) as an effective method for vaccinating against gram-negative infections.

What is claimed is:

1. A vaccine for use in immunizing an animal against an infection by a gram-negative bacteria, said vaccine comprising:
   (a) at least four siderophore receptor proteins extracted from an outer membrane of at least two different serotypes of bacteria of the Pasteurellaceae family;
   (b) a non-iron-regulated outer membrane protein extracted from a bacteria selected from the group of bacteria in the families of Enterobacteriaceae and Pasteurellaceae and, having a molecular weight of about 34–38 kDa; and
   (c) a physiologically acceptable carrier.

2. The vaccine according to claim 1, comprising 5–15 siderophore receptor proteins.

3. The vaccine according to claim 1, comprising a siderophore receptor protein reactive with a siderophore selected from the group consisting of aerobactin siderophore, coprogen siderophore, enterochelin siderophore, citrate siderophore, multocidin siderophore, and ferrichrome siderophore.

4. The vaccine according to claim 1, effective to stimulate production of antibody to the siderophore receptor protein in an adult animal and subsequent transfer of said antibody to progeny of the adult.

5. The vaccine according to claim 1, wherein the carrier is a liquid, and the amount of the siderophore receptor protein in the vaccine is about 25–5000 μg/ml.

6. The vaccine according to claim 5, wherein the carrier is selected from the group consisting of physiological saline, phosphate-buffered saline, Tris(hydroxymethyl aminomethane), and Tris-buffered saline.

7. The vaccine according to claim 1, wherein the carrier is in the form of a solution, water-in-oil emulsion, liposomes, or a metabolizable solid matrix.

8. The vaccine according to claim 1, further comprising an adjuvant selected from the group consisting of aluminum hydroxide, aluminum phosphate, and Freund's Incomplete Adjuvant.

9. The vaccine according to claim 1, wherein the siderophore receptor protein is capable of stimulating production of an antibody reactive with a fungus selected from the group consisting of Aspergillus flavus, Penicillium spp. and Fusarium spp.

10. The vaccine according to claim 1, wherein the siderophore receptor proteins are obtained from a population of bacteria isolated from a population of animals.

11. The vaccine according to claim 10, wherein the siderophore receptor proteins are derived from 3–200 field isolates.

12. The vaccine according to claim 1 wherein the siderophore receptor proteinS have molecular weight of about 80–96 kDa.

13. The vaccine according to claim 12, wherein the siderophore receptor protein extracted from the bacteria of the Pasteurellaceae family has a molecular weight of about 96 kDa, 84 kDa, or 80 kDa as determined by SDS-PAGE.

14. A method for immunizing an animal against an infection by a gram-negative bacteria, comprising:
   (a) administering to the animal a vaccine comprising:
      (i) at least four siderophore receptor proteins extracted from an outer membrane of at least two different serotypes of bacteria of the Pasteurellaceae family;
      (ii) a non-iron-regulated outer membrane protein extracted from a bacteria selected from the group of bacteria in the families of Enterobacteriaceae and Pasteurellaceae and, having a molecular weight of about 34–38 kDa; and
      (iii) a physiological acceptable carrier.

15. The method according to claim 14, wherein the vaccine is administered by subcutaneous injection, intramuscular injection, sustained release repository, aerosolization, or inoculation into an egg.

16. The method according to claim 14, wherein the vaccine induces an effective antibody titer to prevent or eliminate the infection without administration of a booster of the vaccine.

* * * * *

UNITED STATES PATENT AND TRADEMARK OFFICE
CERTIFICATE OF CORRECTION

PATENT NO. : 5,830,479

DATED : NOVEMBER 3, 1998

INVENTOR(S) : EMERY ET AL.

It is certified that error appears in the above-identified patent and that said Letters Patent is hereby corrected as shown below:

Col. 14, line 48: "250°C" should read —25°C—

Col. 26, line 25, claim 12: "proteinS" should read —proteins—

Signed and Sealed this

Twenty-seventh Day of June, 2000

Attest:

Attesting Officer

Q. TODD DICKINSON

Director of Patents and Trademarks